(12) United States Patent  
Leiner et al.

(10) Patent No.: US 8,158,438 B2  
(45) Date of Patent: Apr. 17, 2012

(54) METHOD FOR THE DETERMINATION OF THE CONCENTRATION OF A NON-VOLATILE ANALYTE

(75) Inventors: Marco Jean-Pierre Leiner, Graz (AT); James Kenneth Tusa, Alpharetta, GA (US)

(73) Assignee: Roche Diagnostics Operations, Inc., Indianapolis, IN (US)

( * ) Notice: Subject to any disclaimer, the term of this patent is extended or adjusted under 35 U.S.C. 154(b) by 978 days.

(21) Appl. No.: 11/994,548

(22) PCT Filed: Jul. 4, 2006

(86) PCT No.: PCT/EP2006/006487  
§ 371 (c)(1),  
(2), (4) Date: Mar. 14, 2008

(87) PCT Pub. No.: WO2007/006454  
PCT Pub. Date: Jan. 18, 2007

(65) Prior Publication Data  
US 2008/0215254 A1    Sep. 4, 2008

(30) Foreign Application Priority Data

Jul. 7, 2005 (EP) .................................... 05450117

(51) Int. Cl.  
*G01N 21/76* (2006.01)

(52) U.S. Cl. ............ 436/172; 436/50; 436/164; 436/74; 436/11; 436/546; 422/82.05; 422/64; 435/970; 435/805; 435/7.1; 600/317; 702/25; 356/243.2

(58) Field of Classification Search .................. 436/50, 436/74, 164, 172; 422/82.05  
See application file for complete search history.

(56) References Cited

U.S. PATENT DOCUMENTS 5,166,079 A * 11/1992 Blackwood et al. .......... 436/546

OTHER PUBLICATIONS

Mills et al. Topics in Fluorescence Spectroscopy vol. 9, 2005, DOI: 10.1007/b101259.*  
Tusa et al. Journal of Materials Chemistry, vol. 15, May 13, 2005, pp. 2640-2647.*

* cited by examiner

*Primary Examiner* — Sally Sakelaris  
(74) *Attorney, Agent, or Firm* — Dinsmore & Shohl LLP

(57) ABSTRACT

The invention relates to a method for the determination of the concentration of a non-volatile analyte in an aqueous sample medium, with the use of an optical sensor which contains a luminescent dye and is calibrated at the user site by means of a single-point-calibration. To enable the user to completely dispense with all calibration media a luminescence measurement value is obtained at the user site with the sensor in contact with the aqueous or bloodlike sample medium, which value is referenced to the relative characteristic obtained at the factory site and to a measured dry calibration value obtained at the user site, the concentration of the non-volatile analyte being deduced from these data.

14 Claims, 6 Drawing Sheets

METHOD FOR THE DETERMINATION OF THE CONCENTRATION OF A NON-VOLATILE ANALYTE

FIELD OF THE INVENTION

The invention relates to a method for the determination of the concentration of a non-volatile analyte present in an aqueous sample medium with the use of an optical sensor which contains a luminescent indicator dye whose luminescence depends on the concentration of the analyte and which is calibrated at the user site by means of a single-point-calibration.

BACKGROUND OF THE INVENTION

Analyzers for the determination of non-volatile substances in a liquid (e.g. ionic substances such as $H^+$ (pH), $Na^+$, $K^+$, $Ca^{++}$, $Cl^-$, neutral or charged molecules such as glucose, urea or lactate) are used in medical, environmental, and industrial technology. Clinical diagnosis, in particular, relies heavily on analyzing equipment for the determination of so-called "critical care analytes" in biological fluids such as urine, plasma, serum and above all whole blood. Such systems frequently comprise diverse sensing elements for determining the respective parameters. Such sensing elements may be used for a single determination (single-use) or reused for multiple determinations (multiple-use).

Sensing elements of this kind often utilize electro-chemical sensing technologies or optical-chemical sensing technologies for the determination of gas parameters, pH-values, ionic values or metabolite values in clinical diagnostics. Preferably a plurality of sensing elements for the determination of diverse analytes are bundled into a "cartridge" (see for instance Ann. Biol. Clin. 61, 183-91, 2003).

Clinical diagnosis requires a high degree of accuracy of measurement results. In addition, a single measurement step should supply measurement values for a large number of substances. It is furthermore expected that measurement results are presented with minimum delay and that cost per measurement value is low. Often it is desirable that measurements be performed in close proximity to the patient, for instance "at the bedside", in the physician's office or in the critical care unit.

As a consequence, time-consuming calibrating procedures involving various calibrating media prior to actual measurement will not be acceptable, especially when "single-use" sensors are concerned. Since the cost of miniaturized devices and sensing elements must be kept low, procedures requiring costly apparatus, complex sensing elements, or a plurality of fluids and other supplies are unsatisfactory.

Electrochemical sensors may be based on one of several different measurement principles, such as potentiometric, amperometric or conductometric measurement principles. All principles require the use of a reference electrode and are often applied in configurations requiring contact with a wet calibration fluid prior to measurement of the unknown sample.

U.S. Pat. No. 4,734,184 (Burleigh et al.) discloses an electrode assembly for monitoring the concentration of a number of gases and ions present in the blood. Although the assembly is stored dry to promote an extended shelf-life, the electrodes are thoroughly hydrated (wet-up) prior to use.

U.S. Pat. No. 4,654,127 (Baker et al.) discloses a sensing device equipped with species-selective sensors and a rotatable multichamber reservoir in which calibrant and sample solutions are contained but in separate chambers. A plurality of chemical species may be detected by this device. Furthermore, these commercially available sensors are stored in a high humidity package (i.e., substantially wet). This packaging method has the effect of limiting the shelf-life of these sensing devices.

U.S. Pat. No. 5,112,455 (Cozette et al.) discloses a sensing device equipped with a reference electrode and at least one substantially dry-stored sensor capable of exhibiting a response to changes in the concentration of a preselected analyte species before the sensor attains full equilibrated wet-up. However the sensor and reference electrode must contact a calibrant fluid before the electrodes attain an equilibrated "wet-up" state, to derive meaningful analytical information from such solid-state electrodes.

Optical-chemical sensors may be based on one of several different optical measurement principles, such as fluorescence, absorbance, or reflectance measurement principles. They are applied in a number of very diverse measurement configurations and, in contrast to electro-chemical sensors, optical sensors typically do not require a reference electrode or reference sensor.

An optical-chemical or optical-biochemical sensor typically consists of one or more layers of inorganic and/or organic, preferably polymeric, substances applied on a transparent carrier or substrate, with a least one layer containing a dye whose optical characteristics (absorption, luminescence) vary with the concentration of a particular analyte contained in a sample medium. Optical-biochemical sensors contain at least one biochemical or naturally-occurring biotic agent, for instance an enzyme. The carrier may be planar, cylindric, or of any other shape. For example the layers may be applied to the "wells" of micro-titration plates, at the tip of optical fibre bundles or on single optical fibres or light-guiding structures.

An optical-chemical sensor is usually able to measure reversibly and often continuously. Exceptions to this rule are certain enzyme-carrying biochemical sensors. These measure discontinuously and often consume a substrate or reactant (such as oxygen), i.e. they or their substrate or reactant are consumed or altered and must be regenerated for subsequent measurements. Since sensors generally have a limited lifetime, they must be replaced at certain intervals.

An optical-chemical sensor is placed in direct contact with the sample medium and, when exposed to light, provides optically readable information about a particular analyte of interest which is present in the sample medium (e.g. concentration, activity or partial pressure).

The majority of optical-chemical sensors require several calibration measurements with calibrating media, with the analyte concentrations being distributed over the whole measurement range. The number of calibration measurements required depends on the measurement accuracy desired in the relevant measurement range, accuracy and range varying for different applications. For example measurements of physiologic sodium levels in blood typically span at least 120 to 160 millimoles per liter and hence require calibration measurements within that range.

In order to minimize the number of calibration measurements, at least as far as the user is concerned, and to make them fast and simple, it is possible to obtain one or more of the sensor characteristics at the manufacturing site (e.g. by calibrating a production batch or lot), and to provide the relevant data together with the sensors in suitable form.

State-of-the-art devices occasionally use the term "calibration-free sensors" in their documentation. In reality there is no such thing as a calibration-free sensor. A new sensor or newly designed or developed sensor is calibrated at least once, or one or more of its characteristics are measured at least once. It is for instance possible to calibrate a production batch during sensor fabrication and subsequently to produce sensors with just this known characteristic by reproducible fabrication techniques. Furthermore it is possible to calibrate at least one sensor or a representative number of sensors of a batch and to assign the measured characteristics to all sensors of this batch. This requires sufficiently reproducible fabrication within a batch and/or reproducible fabrication of sensors between batches. It also requires reproducible fabrication of any measuring devices or instruments supplied or endorsed by the manufacture to perform the measurement. Such factory calibration is both time-consuming and expensive, requiring extremely tight control over sensor characteristics and concomitant control over the characteristics of the measuring device or instrument.

A number of solutions have been proposed in this context, for instance measuring luminescence intensity at a plurality of wavelengths, or measuring luminescence decay time of optical sensors by methods of time- or phase-resolution. As described below, very often a multiplicity of methods are applied within a single system, due to the scarcity of indicator molecules responsive to all desired analytes within their respective concentration ranges.

For example one such "calibration-free" system utilizing optical-chemical sensors is proposed for "near-patient-testing" of blood gases ($PO_2$ and $PCO_2$) and blood pH-value in Clin. Chim. Acta 307, 225-233, 2001. In this system the determination of $PO_2$ is carried out by measuring the luminescence decay time of a luminescent dye immobilised on a membrane. $PCO_2$ is determined—avoiding the use of an optical sensor—by means of the direct infrared absorption of $CO_2$. The pH-value is determined calorimetrically (using the principle of absorbance) through multi-wavelength transmission measurement of a calorimetric pH-indicator dye immobilised on a membrane with the sample removed. Such systems employing multiple methods are often complex and expensive.

Measuring the oxygen content of a blood sample by a luminescence quenching method is also known from U.S. Pat. No. 5,564,419 (Radiometer). The method uses a luminophore whose luminescence is quenched in the presence of oxygen. The $PO_2$ of the sample is determined by measuring the decay time of the luminescence.

In contrast to the measurement of luminescence decay time, the determination of luminescence intensity poses greater problems as regards the parameters of the components of the optical system. For sensors using luminescence indicators with long decay times (>500 nanoseconds) state-of-the-art requirements concerning the optical measurement set-up are relatively mild.

Unfortunately there are a large number of analytes, especially ions and metabolites, for which no simple indicators or indicator systems with long luminescence decay times are available. With increasing luminescence life-time of the indicator the cross-sensitivity against well-known quenching substances, especially $O_2$, will also increase. Indicators with decay times less than 100 nanoseconds (ns) are less affected by such problems, however the accurate and calibration-free determination of such small decay times usually requires more costly and complex instrumentation. Modern medicine increasingly requests low-cost, rugged, and miniaturized analyzers which may be used in close proximity to the patient.

The determination of the pH-value of a blood sample by a colorimetric method is known from U.S. Pat. No. 5,288,646 (Radiometer), where a photometric measurement is proposed using a calorimetric (non-luminescent) pH-indicator dye which is immobilised on a membrane situated on the channel-wall of a "sampling device". Transmission measurement using multiple analysis wavelengths is costly and requires measures to correct for variations of the characteristics of the optical components and of the light paths. Since blood absorbs light the sample must be removed from the light path prior to measurement, for instance by compressing the channel.

In the context of luminescence indicators it has been proposed (see U.S. Pat. No. 5,108,932 (Wolfbeis)) to illuminate at one wavelength, preferably at the isosbestic point, and to measure at two different wavelengths of light emission. Working with multiple wavelengths or detection at multiple wavelengths with the characteristics of the optical components fully known demands costlier technology however. In contrast to the measuring of pH-values there is a large number of analytes for which no luminescence indicators suitable for multiple wavelength methods are available.

Measuring luminescence intensity at one broad band of analytical wavelengths is particularly advantageous. In comparison with the technologies mentioned above measuring luminescence intensity has the advantage that the set-up of optical and electronic components necessary for measurement is relatively simple and may be realized with low-cost components. A disadvantage here is the fact that certain parameters of the optical components of the measurement set-up and of the individual sensors, which influence luminescence intensity, will affect the measurement result. Although it is basically possible to build optical systems and sensors with stable components and sensors whose characteristics are precisely determined, this will be unrealistic in view of the above requirements and the expense and costs involved. A solution of the problem, which is known in principle, consists in performing a single-point calibration immediately prior to the measurement in which the parameters are determined which depend on the individual measuring equipment set-up and on the individual sensor element and which influence the luminescence intensity.

According to the state of the art it is possible, for instance in the case of optical sensors based on the measurement of luminescence intensity at a broad band of analytical wavelengths, to obtain a relative characteristic (i.e. a characteristic not depending on the individual measuring system) by calibration measurements during manufacturing and to supply this characteristic, in the form of parameters (coefficients) of a mathematical equation describing the characteristic curve, together with the sensor for use in the measuring system at the user site. The parameters may be supplied in the form of bar-codes, or stored on electronic, magnetic or optical storage media. For determination of the characteristic valid in the user measurement system (i.e. the effective characteristic) at least one further measurement of luminescence intensity is required. According to the state of the art this is obtained as follows: by means of a calibration medium containing at least the analyte to be measured in known concentration, a luminescence value corresponding to this known concentration is set at the sensor of the user measurement system and luminescence is measured, giving a calibration value for the user site. The relative characteristic referenced on the calibration value at the user site will yield the effective characteristic.

For a simple optical-chemical sensor system, in which the luminescence indicator is electronically excited by irradiation with light in an absorption band and the intensity of the emitted light in an emission band is used for determination of the analyte, at least one calibration measurement performed at the user site is required.

Regarding this user-site calibration, measurement procedures and devices are known for single-use measuring elements containing one or more optical-chemical sensors and a calibration medium.

In U.S. Pat. No. 5,080,865 (Leiner) a single-use measuring element is proposed which contains one or more electrochemical or optical sensors and includes a calibration medium suitable for the given sensor(s). Prior to measurement the measuring element is inserted into the analyzer and a calibration measurement followed by the sample measurement is performed. If a liquid tonometered with one or more gases (e.g. $O_2$ and $CO_2$) is used, gas- and ion-sensors may be calibrated simultaneously. Storing the sensors in a liquid has the advantage that the sensors are ready for use immediately after measurement temperature has been reached. The disadvantage is that the "shelf-life" of the sensors is limited to several months when they are stored in a liquid. This is the case especially for very sensitive, enzyme carrying biosensors. A further disadvantage lies in the fact that the single-use measuring element must hold the liquid without loss during shelf-life and that a fluidic system for transport of the calibration liquid must be provided.

In U.S. Pat. No. 5,351,563 (Karpf) it is proposed to integrate a liquid storage medium (which at same time is a calibration medium for pH- and ion-sensors) into the single-use measuring element. The storage medium is displaced by a calibrating gas saturated with water vapour, following which calibration and subsequently sample measurement are performed.

U.S. Pat. No. 5,166,079 (Blackwood et al.) discloses a method and test device for competitive immunoassays using binding partners which are labelled with a fluorescent moiety. In the dry state, the reagent layer of the test device comprises an immunocomplex of an immobilized binding partner (e.g. an antibody) for the analyte (e.g. antigen) of interest and a conjugate of a labelled analyte. In practice, the label which is present in the reagent layer is optically read prior to applying the sample to the assay element. When sample liquid containing the analyte of interest has been added to the test device, the analyte present in the sample competes with the labelled analyte conjugate in the reagent layer for the available binding sites on the immobilized binding partners. The labelled analyte dissociates therefrom and is replaced by the sample analyte in a ratio appropriately equal to the relative amounts of sample analyte and labelled analyte. A second readout signal of the reagent layer is obtained when the sample has been applied which signal is inversely proportional to the amount of analyte in the sample. The ratio of the second signal to the first signal is taken and compared with that for known amounts of analyte to determine the amount of analyte in the sample. According to U.S. Pat. No. 5,166,079, the method disclosed therein allows to compensate for variations in the instrument and in the thickness of the reagent layer from element to element and yields a better precision. Importantly, the method of U.S. Pat. No. 5,166,079 is based on the displacement of fluorescent labelled analyte from the layer which is interrogated by radiation, but the analyte in the sample does not affect the fluorescent properties of the fluorescent moiety as such.

Accordingly, there remains at the present a need for a method which integrates a sensing device, preferably an optical-chemical sensor, having the requisite of long shelf life, predictable and reproducible optical response and "wet-up" characteristics, which method allows to obtain cost-effective and accurate determinations of the concentration of analytes. Such determinations are desirably made in five minutes or less, most preferably within about a minute.

Basic Principles

To enable better understanding of the present invention the relationship between the intensity S of the luminescence signal of a luminescent species A, its concentration cA and the parameters of the given measuring system will be summarized and wet calibration, known in the art, will then be described using the case of an optical sensor with an intramolecular charge transfer (ICT) dye for determination of the pH-value of a sample.

To conform with published equations concerning wet calibration the letter S was used to designate luminescence intensity. In contrast thereto, the description of the invention will use the letter L for luminescence intensity in equations and their derivation.

Parker's equation describes the relationship between luminescence intensity S of a species A and its concentration cA when excitation wavelength (ex) and emission wavelength (em) are given:

$$S = I_0 k_{ex} e k_{em} \epsilon \Theta d cA \quad (a)$$

where $I_0$ is the intensity of the light source, $k_{ex}$ and $k_{em}$ are transmission parameters of the optical components on the excitation or the emission side, and e is the sensitivity of the detector, all depending on the light wavelength $\lambda$. Photophysical parameters depending on the luminescent species are the molar absorption coefficient $\epsilon$, the luminescence quantum yield $\Theta$ and the analyte concentration cA. d is the mean pathlength of light in the medium containing the species.

For a given species A the product of the parameters $I_0$, $k_{ex}$, e, $k_{em}$, $\epsilon$, $\Theta$ and d may be combined into a new parameter $k_A$ $$k_A = I_0 k_{ex} e k_{em} \epsilon \Theta d \quad (b)$$

resulting in $$S = k_A cA. \quad (c)$$

The properties of optical components (e.g. intensity and spectrum of the light source, spectral transmission properties of optical filters, spectral sensitivity of detectors, etc.) and of optical assemblies (length of light paths) vary within certain limits and over time. This will cause the parameter $k_A$ to have a certain variance between sensors and between devices which will also change over time (duration of operation). These variances must be taken into account when measurements requiring a high degree of accuracy and reproducibility are made. Minimizing these variances is costly and therefore economically not feasible where low-cost measuring systems are concerned.

A well-known optical-chemical sensor for pH-determination uses the ICT dye hydroxy-pyrene-trisulfonic acid (HPTA) (Ann. Biol. Clin. 61, 183-91, 2003).

The calibration curve of the sensor can be derived from the mass action law's simple relationships between pH-value and the concentration of the protonated (AH) and deprotonated (A−) dye species:

$$pH = pK + \log(cA^-/cAH) \quad (d)$$

When excited near 470 nm in an aqueous environment, no luminescence at 520 nm is generated from the protonated form. The total concentration cD of the dye is the sum of the concentrations of the individual dye species:

$$cD = cA^- + cHA \quad (e)$$

At high pH-values (i.e., pH>pK+3), the protonated dye species is absent. Thus, at high pH-values $cD = cA^-$.

Substitution of cHA in eqn. (d) by the expression cHA=cD−cA⁻ generated from eqn. (e) and simplification yields the equation:

$$\frac{cA^-}{cD} = \frac{1}{1+10^{pK-pH}} \quad (f)$$

Eqn. (f) is equivalent to equation (g)

$$\frac{k_A cA^-}{k_A cD} = \frac{1}{1+10^{pK-pH}} \quad (g)$$

and further equivalent to equation (h) in view of equation (c)

$$\frac{S}{S_m} = \frac{1}{1+10^{pK-pH}} \quad (h)$$

where S denotes the luminescence intensity at a given pH-value and $S_m$ denotes the luminescence intensity in absence of the protonated species HA. Finally, rearrangement of eqn. (h) yields the calibration curve of the sensor (published in Ann. Biol. Clin. 61, 183-91, 2003.)

$$S = \frac{S_m}{1+10^{pK-pH}} \quad (i)$$

The calibration curve (eqn. i) is a sigmoidal function characterized by increasing luminescence intensity in going from low to high pH-values and a point of inflection (the dye's pK-value) centred at mid-physiologic pH-values, where S is the relative luminescence intensity as a function of pH, $S_m$ is the maximum intensity seen at high pH-values and pK is the negative log of the indicator's proton dissociation constant.

Solving equation (i) for pH gives $$pH = pK - \log\left(\frac{S_m}{S} - 1\right) \quad (j)$$

from which the pH-value may be computed if the parameters S, $S_m$ and pK are known.

To determine the pH-value the luminescence intensity S is obtained at the user site from the luminescence measurement value of the sensor in contact with the aqueous sample. The pK value is obtained by factory calibration. The value $S_m$ at the user site is unknown and must be determined at the user site from the luminescence measurement value of the sensor in contact with an aqueous calibrating solution of known pH-value. The necessity of the determination of $S_m$ at the user site is obvious from equation (g). The parameters $k_A$ in the numerator and denominator of the fraction are identical only if the quantities making up the parameters $k_A$ are equal. These quantities can be seen from (b). Equality will essentially hold if $S_m$ is determined shortly before or after S is determined using one and the same measurement set-up.

$S_m$ may for instance be determined at the user site by measuring the luminescence of the sensor in contact with an aqueous calibration medium with high pH-value.

Preferably $S_m$ is obtained by measuring the luminescence intensity $S_{cal}$ of the sensor in contact with an aqueous calibration medium, whose pH-value ($pH_{cal}$) is close to the pK value known from factory calibration, and by computing $S_m$ from equation (k):

$$S_m = S_{cal}(1+10^{pK-pHcal}). \quad (k)$$

U.S. Pat. No. 6,211,359 (He et al.) discloses similar characteristics for optical sensors for the determination of potassium with luminescent indicators based on the photo induced electron transfer (PET) effect. Equation 6 of U.S. Pat. No. 6,211,359 (He et al.) may also be applied in the case of other ions and in addition takes into account interfering ions which might be present. Equation 7 of U.S. Pat. No. 6,211,359 is used to obtain the concentration of the ion to be measured in analogy to eqn. (j). Eqn. 8 of U.S. Pat. No. 6,211,359 is used to find the unknown value of $S_m$ by means of a single-point calibration in analogy to eqn. (k).

U.S. Pat. No. 6,171,866 (He et al.) discloses similar characteristics for optical sensors for the determination of calcium with luminescent indicators based on the PET effect. Eqn. 6 of U.S. Pat. No. 6,211,359 and eqn. 4 of U.S. Pat. No. 6,171,866 are equivalent with the exception that eqn. 4 does not take into account interfering ions and that the concentration and the $K_d$ value are given in logarithmic form.

Definitions

In order to prevent misunderstandings due to varying definitions in previously published documents the following definitions are given for a number of essential concepts.

Analyte: in the following analyte will mean a substance in an aqueous sample medium to be qualitatively or quantitatively determined. The term non-volatile analyte will be used in distinction from volatile analytes, i.e. substances which are gaseous under standard conditions such as $O_2$ or $CO_2$. Non-volatile analytes include, e.g. ionic substances such as $H^+$ (pH), $Na^+$, $K^+$, $Ca^{++}$, $Cl^-$, neutral or charged molecules such as glucose or lactate. The interaction between analyte and luminescent dye in the optical sensor can either be direct or indirect.

"Direct interaction" means that the analyte reaches the dye and both species actually react with each other.

"Indirect interaction" means that the analyte does not come into direct contact with the luminescent dye and/or that the luminescent response of the dye is not due to chemical or physical analyte-dye interaction. Examples are furnished by enzymatic sensors which belong to the group of biochemical sensors. In this context one or more enzymes react with the analyte, yielding a reaction product which in turn reacts directly with the indicator dye. In certain known biosensors the enzyme reaction causes e.g. a change in pH-value which may be determined by means of a pH-sensitive indicator dye. Examples may be found in Biosensors & Bioelectronics 10, 1995, 653-659 (Konicki et al.).

Another type of indirect interaction occurs in assays based on the fluorescence resonance energy transfer (FRET) principle (cf. infra) according to which the analyte interacts with an acceptor dye and the luminescence of a donor dye is measured.

Irrespective of whether a direct or indirect interaction of the analyte with the luminescent dye occurs, in analogy to classical pH absorption dyes these luminescent dyes are subsequently called luminescent indicator dyes.

Unless specifically mentioned, the term "analyte" in connection with its interactions with the luminescent dye shall encompass both the direct and indirect interactions as defined supra. E.g. if the non-volatile analyte is $H^+$ and a pH-sensitive dye is used, direct interaction of the analyte and the dye occurs. If, however, glucose is the analyte and an enzyme sensor is used employing the principle of detecting a pH change which occurs when glucose is enzymatically converted, the species interacting with the dye is $H^+$, not glucose.

In the present context, therefore, the statements like "the analyte reacts with the indicator dye", "the analyte interacts with the indicator dye" "the analyte is bound to the dye" and similar statements shall encompass both direct and indirect analyte—dye—interactions as defined supra.

Sample medium: the sample medium typically is an aqueous solution with dissolved salts, which in addition may contain organic, biochemical or biological components. The sample media to be measured may come from the area of environmental technology (water or waste-water samples), from biotechnology and from medicine (blood, serum, plasma, urine samples or samples of other body fluids).

Optical sensor: in the usage of the present invention the term "optical sensor" refers to the interface between a sample medium and the optical components of a measuring device; in particular, it refers to one or more layers of inorganic and/or organic, preferably polymeric, substances applied on a transparent carrier or substrate, with at least one layer containing a dye whose optical characteristics (absorption, luminescence) vary with the concentration of a particular analyte contained in a sample medium. This interface is also designated as optode or optrode.

Components of the measuring system or the measuring device, such as light source, detector, optical filters, electronic signal amplifiers and the evaluation unit are not part of the optical sensor.

The present invention relates to optical sensors for the measurement of substances that are non-volatile (non-gaseous) under standard conditions, such as inorganic ions (e.g. $H^+$, $Na^+$, $K^+$, $Ca^{++}$, $Cl^-$, $NO_3^-$, $Fe_2^+$, etc.), electrically neutral or charged molecules (e.g. lactate, glucose, urea, creatinine, amines, alcohols) dissolved in preferably aqueous sample media.

The present invention does not relate to optical sensors for the measurement of substances that are gaseous under standard conditions such as $O_2$, $CO_2$, $SO_2$, etc. In particular, it does not relate to optical gas sensors, i.e. sensors which in the dry state and in contact with a gaseous sample medium respond to a change in the partial pressure of the analyte (e.g. $O_2$, $CO_2$) with a change in the optical signal. The invention does also not relate to sensors for such volatile analytes dissolved in an aqueous sample that is in contact with the sensor.

However, the present invention can be used when separate sensors for non-volatile and volatile analytes are used in combination. In this case, however, the invention is applicable only in connection with the sensors for non-volatile analytes.

Luminescence-optical sensors: the present invention preferentially relates to luminescence-optical sensors. Such sensors contain at least one luminescent dye (also referred to as luminescent indicator dye) in at least one layer.

Dry optical sensor: the term relates to an optical sensor according to the above definition, in which all sensor materials making up the sensor are dry (i.e. essentially free from water). The sensor is in this state during storage and/or prior to measurement use. To functionally activate the sensor it must be brought into contact with water or a medium containing water, for instance an aqueous activation medium, a sample medium, or a calibration medium.

Wet optical sensor: the term relates to an optical sensor according to the above definition which is in contact with an aqueous medium, for instance an aqueous activation-, sample-, or calibration-medium.

Activity: the activity a of an ionic substance is the product of its concentration c and its coefficient of activity Activity depends on ionic strength. At low ionic strength the activity coefficient is 1, and thus c=a. Depending on the application the expert will compute a suitable other value, e.g. by using the equations of Debeye-Huckel. If, in the following, the determination of the concentration is mentioned, the determination of the activity is also encompassed.

Measuring system: the term relates, with the exception of the optical sensor itself as defined above, to all optical, electronic and mechanical components which are required for application of the optical sensor, such as the light source generating the excitation radiation, the detector measuring the intensity of the measurement radiation, optical filters, electronic signal amplifiers, the evaluation unit and the measuring cell (for instance a cuvette to whose wall the sensor is attached, a cell with an inlet and possibly an outlet and a measuring passage to whose wall the sensor is attached, or a micro-titration plate).

Measuring device or device: the totality of all the components of the measuring system. Preferably, the measuring cell (containing the optical sensor) is not an integral part of the device but may be replaced together with the sensor.

(Response) characteristic or characteristic function: the characteristic describes the functional relationship between the measured intensity of the measurement radiation (e.g. the luminescence intensity) and the concentration or activity of the analyte to be determined.

In the case of optical sensors the characteristic is non-linear, i.e. the functional relationship between luminescence intensity and concentration of the analyte over the complete dynamic measurement range cannot be represented by a straight line with sufficient accuracy. Depending on the required width of the measurement range and on the required degree of accuracy it may be possible for certain applications to represent at least parts of the characteristic by straight lines.

The characteristic is determined by measuring the luminescence of the sensor for a series of aqueous calibration media with different, known concentrations of the substance to be determined, these known concentrations being distributed over the expected range of concentrations of the analyte to be determined. From these measured calibration values the characteristic is derived in the form of a table or a diagram, preferably in the form of a mathematical equation. In actual measurement the concentration of the analyte is computed using the luminescence intensity measured in contact with the sample and the characteristic function.

Effective characteristic: the characteristic valid for a given sensor together with a given measuring system. Referencing the effective characteristic obtained by a factory-site measuring system to a calibration value obtained by the factory-site measuring system results in the relative characteristic.

Relative characteristic: means a characteristic independent of the specific measuring system. The relative characteristic referenced to a calibration value obtained for a user-specific measuring system provides the effective characteristic valid for the user-specific measuring system. Typically, the relative characteristic is obtained at the factory-site (cf. also the definition for "Effective characteristic", supra) and can be referenced to a wet or a dry calibration value (cf. also the definition for "Wet to dry relationship", infra).

Effective and relative characteristics may be computationally transformed one into the other, provided: (a) that for the measuring system for which the effective characteristic is valid, at least one calibration value is known, (for instance the intensity of the measurement radiation of the sensor in contact with a medium of known analyte concentration); and (b) that the measuring systems used for obtaining the effective and the relative characteristic are built alike.

"Wet to dry relationship": In the context of the present application, the "wet to dry relationship" is a relationship which allows computing at the user site the concentration of the non-volatile analyte using the user-site dry calibration value and the luminescence measurement value, both measured at the user site. The "wet to dry relationship" typically is derived from factory-site dry and wet calibration values that are obtained from measurements using a representative number of single sensors from a production batch or lot. These factory-site dry and wet calibration values then lead to the "wet to dry relationship" which is taken as a relationship which is valid for the complete production lot of which the representative sensors came from.

The "wet to dry relationship" can for example be a relative characteristic, or a relative characteristic and a ratio value, and/or the like. In connection with some typical, but not limiting, examples (cf. Examples 1, 1.1., 1.2., 1.3., 2, 2.1., and 2.2., infra) and embodiments, the following specification will show how the determination of the concentration of a non-volatile analyte can be carried out using the "wet to dry relationship".

With reference to Example 1, in particular Examples 1.1., 1.2., and 1.3. (infra), the "wet to dry relationship" comprises a relative characteristic referenced to a wet calibration value obtained at the factory-site and a ratio value.

With reference to Example 2.1. (infra), the "wet to dry relationship" comprises a relative characteristic referenced to a dry calibration value obtained at the factory-site.

With reference to Example 2.2. (infra), the "wet to dry relationship" comprises a relative characteristic referenced to a dry calibration value based on ratio values obtained at the factory-site.

Calibration: means the determination of the characteristic. When an optical sensor is calibrated it is brought into contact with calibrating media in a measuring system, which media contain the analyte to be measured in different, known concentrations. The optically measurable response of the sensor, e.g. the luminescence intensity, referenced to the known concentration of the analyte in the calibration medium serves as a reference value for the unknown concentration of the analyte in a sample to be measured.

Prior to sample measurement the sensor may be wet or dry. If dry, it must be activated by the calibration medium. In this case the calibrating medium is also the activation medium. It is also possible to use a storage medium, if provided, as the activating and also calibrating medium. Examples for this may be found U.S. Pat. No. 5,080,865 A and in U.S. Pat. No. 5,658,451 A.

Single-point-calibration: a luminescence measurement value of the dry sensor is obtained and taken as a calibration value. From the calibration value obtained with the given measuring system and the relative characteristic obtained from a measuring system built in the same way the effective characteristic valid for the given measuring system can be derived.

Measurement and evaluation: during measurement the optical sensor is brought into contact with the sample medium, which contains the analyte in a concentration to be determined. The concentration of the analyte is found from the sensor signal measured (e.g. luminescence intensity) with reference to the effective characteristic of the optical sensor.

Factory-site calibration: the determination of the parameters of the characteristic (if eqn. 7, cited below, is used, for instance parameters $K_d$ and q) at the factory site with the exclusive use of aqueous calibrating media is well-known and not subject of the present invention.

If some calibration steps are carried out already at the factory site using a suitable measuring system, only one calibration step (single-point-calibration) may be needed at the user site, provided a measuring system of identical design is used. A necessary condition for factory-site calibration is that the characteristic obtained at the factory site does not change until the sensor is used (or at least does not change in an unforeseeable way); changes could for instance occur during transport or during storage due to temperature effects or due to chemical or physical ageing or decomposition.

Luminescent indicator dyes: in the given context the term luminescent indicator dye, luminescent dye or luminescence-optical dye refers to all substances whose luminescent response (e.g. luminescence intensity, luminescence decay time) depends on the concentration or activity of the analyte via direct or indirect interaction.

Typically, the luminescent indicator dye is immobilized in an optical sensor, preferably in at least one sensor layer.

Depending on the type of dye or dye-system the luminescent response caused by the analyte concentration is affected by very different chemical-physical and/or photophysical mechanisms. The most important types of dyes are:

A) PET dyes
B) ICT dyes
C) FRET systems (energy transfer systems).

As already defined supra, "direct interaction" means that the analyte reaches the dye and reacts with it.

"Indirect interaction" means that the analyte does not come into direct contact with the luminescent dye and/or that the luminescent response of the dye is not due to chemical or physical analyte-dye interaction.

PET dye: an indicator dye whose luminescence is wholly or partly quenched by photoinduced electron transfer (PET). Luminescence quenching will reduce luminescence quantum yield, luminescence intensity and luminescence decay time.

The electron transfer in a PET indicator dye takes place from an electron donor to an electronically excited electron acceptor. Donor and acceptor are covalently linked via a spacer. The spacer's function is to electronically decouple donor and acceptor. The acceptor is a luminescent substance. The donor is a receptor which is able to bind the analyte, preferably reversibly. If the bound substances are ionic substances the reactive component is also called the ionophore. In a thermodynamic equilibrium reaction the analyte reacts reversibly with the indicator dye by binding to the receptor.

From the luminescence properties (e.g. luminescence intensity, luminescence decay time) the concentration of the analyte may be inferred, for instance by evaluating the visible, or with photo-detectors measurable, intensity of the emitted light in the ultraviolet (UV), visible (VIS), or near infrared (NIR) range.

PET indicator dyes have at least one species A to which the analyte S is not bound, and at least one species B to which the analyte S is bound, the two species and the analyte being in thermodynamic equilibrium after a certain time. In the species B the PET effect is wholly or partly blocked through the binding of the analyte, which results in the luminescence intensity of B having a maximum. In the species A the PET effect is not blocked resulting in a minimum of its luminescence intensity.

Since the dye component of a PET indicator dye remains essentially unaffected by the binding of the analyte, the expert will recognize a PET indicator dye by the fact that in a given chemical environment the absorption and emission spectra of the dye of both species are essentially equal as regards spectral position. Since the total spectrum results from an addition of the spectra of the two species the binding of the analyte will change the luminescence intensity of the excitation- and emission spectrum.

Examples may be found in AP de Silva et al., Coordination Chemistry Reviews 205, 2000, 41-57 (Review of PET dyes), in He et al., Anal. Chem. 75, 2003, 549-555, FIG. 2 (PET indicator dye for $Na^+$) and in J. Am. Chem. Soc. 125, 2003, 1468-1469, FIG. 3 PET indicator dye for $K^+$).

ICT dye: in contrast to PET indicator dyes there is no electronic decoupling of the two parts (dye and receptor component) in an ICT dye (ICT=intramolecular charge transfer). Since the binding of the analyte substantially changes the chromophore system of the dye component, the expert will recognize ICT dyes by the fact that in a given chemical environment the absorption and emission spectra of the dye component of the two species are different as regards spectral position. Since the total spectrum results from the addition of the spectra of the two species the binding of the analyte will change the relative proportion of the two component spectra in the total spectrum.

Examples may be found in Molecular Probes, Handbook of Fluorescent Probes and Research Products, 2002, $9^{th}$ ed., Ch. 21, FIG. 21.19 (SNARF-4F) and FIG. 21.24 (HPTS).

FRET dye: FRET indicator dye systems (FRET=Fluorescence Resonance Energy Transfer) essentially consist of two dyes, a luminescent donor dye and an acceptor dye. The luminescence of the donor dye is quenched by the acceptor dye via radiation-less energy transfer. Quenching of the luminescence changes luminescence intensity and luminescence decay time. The acceptor dye reacts directly or indirectly with the analyte, thus changing its absorption values (absorption spectrum) and the rate of energy transfer. From the luminescence intensity of the donor dye inferences regarding the analyte can be made. A condition among others for FRET to occur is that the absorption spectrum of at least one species of the acceptor dye overlaps at least partially with the emission spectrum of the donor dye. An advantage of FRET systems lies in the fact that the expert has a choice of many known, non-luminescent indicator dyes (especially pH-sensitive absorption dyes) and that the analyte may be determined via the more sensitive luminescence measurement. Examples may be found in U.S. Pat. No. 5,232,858 A (Wolfbeis et al.), in U.S. Pat. No. 5,942,189 A (Wolfbeis et al.) and in Anal. Chim. Acta, 1998, 364, 143-151 (Huber et al.).

SUMMARY OF THE INVENTION

On the basis of the above methods for determination of the concentration of a non-volatile analyte or the pH-value in an aqueous sample medium, improvements and simplifications are provided by the present invention which permit the determination of the concentration of a non-volatile analyte (including pH-value) at the user site without the use of calibrating media. Typically, the measurement method is based exclusively on measuring the luminescence intensity using only one excitation and emission wavelength or band.

For example, in one embodiment a luminescence measurement value is obtained at the user site with the sensor in contact with the aqueous sample medium, which measurement value is referenced to a wet to dry relationship, e.g. a relative characteristic, obtained at the factory site and to a measured dry calibration value obtained at the user site, and that the pH-value or the concentration of the non-volatile analyte (including pH-value) is deduced from these data.

Thus for the first time a measurement method plus calibration procedure based on measuring luminescence intensity will be realized which will require no calibration media at the user-site even if only one excitation and emission wavelength is used. The invention utilizes the surprising fact that optical sensors for the determination of many non-volatile (non-gaseous) substances may be engineered to use a luminescent dye which exhibits luminescence in the dry state if suitably excited.

Provided in one embodiment is a method for the determination of the concentration of a non-volatile analyte present in an aqueous sample medium with the use of an optical sensor which contains a luminescent indicator dye and which is calibrated at the user site by means of a single-point-calibration, comprising measuring at the user site the luminescence of the dry sensor yielding a user-site dry calibration value, obtaining at the user site a luminescence measurement value of the sensor in contact with the aqueous sample medium, and deducing the concentration of the non-volatile analyte from the luminescence measurement value, a wet to dry relationship obtained at the factory site, and the user-site dry calibration value.

In another particular embodiment, the above method of the invention further comprises a) at the factory site
i. choosing a representative number of dry sensors $S_0$ from a plurality of dry sensors $S_n$ made in the same way;
ii. measuring luminescence of each of the chosen dry sensors $S_0$, yielding factory-site dry calibration values;
iii. subsequently measuring luminescence of each of the chosen sensors $S_0$ in subsequent contact with at least two aqueous calibrating media with known, different concentrations of the non-volatile analyte, yielding factory-site wet calibration values;
iv. obtaining a wet to dry relationship of the sensors $S_0$ from the factory-site wet calibration values and the factory-site dry calibration values, which wet to dry relationship is taken as the wet to dry relationship for all sensors $S_n$ made in the same way;

b) at the user site
i. measuring luminescence of a dry sensor Si from the plurality of sensors Sn made in the same way, yielding a user-site dry calibration value;
ii. obtaining a luminescence measurement value of the sensor $S_1$ in contact with the aqueous sample medium; and
iii. computing the concentration of the non-volatile analyte present in the aqueous sample medium from the luminescence measurement value, the user-site dry calibration value, and the wet to dry relationship obtained at the factory site.

A first variant of the above method comprises a) at the factory site
i. a representative number of sensors $S_0$ is chosen from a plurality of dry sensors $S_n$ made in the same way; (i.e. from a production batch or lot, or even—if the production process is highly reproducible—for all sensors of a kind);
ii. luminescence is measured for each of the chosen dry sensors $S_0$, yielding factory-site dry calibration values;
iii. next, for each of the chosen sensors $S_0$ luminescence is measured using at least two aqueous calibrating media with known, different concentrations of the nonvolatile analyte which calibrating media are subsequently brought into contact with the sensors, yielding factory-site wet calibration values;

iv. from the factory-site wet calibration values a relative characteristic of the sensors $S_0$ is obtained, which is taken as relative characteristic for all sensors $S_n$ made in the same way (i.e. belonging to the same production lot);

v. from the factory-site wet calibration values and the factory-site dry calibration values a ratio-value is derived, which ratio value is taken as a corresponding ratio-value for all sensors $S_n$ made in the same way; and that b) at the user site i. luminescence is measured for one dry sensor $S_1$ from the plurality of sensors $S_n$ made in the same way, yielding a user-site dry calibration value;

ii. a luminescence measurement value is obtained with the sensor $S_1$ in contact with the aqueous sample medium; and iii. the concentration of the non-volatile analyte present in the aqueous sample medium, or the pH-value, is computed from the luminescence measurement value, the user-site dry calibration value, the relative characteristic and the ratio value obtained at the factory site.

The first variant of the invention differs in some further points from the known procedures initially described. Thus during factory-site calibration a ratio-value of the factory-site dry calibration value and the factory-site wet calibration value is obtained in addition to the relative characteristic. At the user site only one measurement of the sensor in dry state is required prior to the actual sample measurement in order to obtain a user-site dry calibration value, which permits the concentration of the non-volatile analyte present in the aqueous sample medium to be determined from the measured luminescence value of the sample together with the relative characteristic and the ratio-value, both determined for the whole production lot of sensors at the factory-site.

Another variant of the invention in which a characteristic is derived from the factory-site wet calibration values, referenced to the dry calibration value, and thus a relative characteristic referenced to the dry calibration value is obtained, differs from the aforementioned variant, from step a) iv. onwards, insofar as at the factory site a relative characteristic for the sensors $S_0$ is obtained from the factory-site wet calibration values and the factory-site dry calibration values, which relative characteristic is taken to be valid for all sensors $S_n$ made in the same way; and at the user site the concentration of the non-volatile analyte present in the aqueous sample medium is computed from the luminescence measurement value, the user-site dry calibration value and the relative characteristic.

This variant of the invention also differs in a number of points from the known procedures initially described. Thus during factory-site calibration a factory-site dry calibration value is obtained, which enters into the computation of the relative characteristic. At the user site only one dry measurement of the sensor is required prior to actual sample measurement in order to obtain a user-site dry calibration value, such that the concentration of the non-volatile analyte present in the aqueous sample medium can be determined from the measured luminescence value together with the relative characteristic obtained at the factory site and the user-site dry calibration value.

A further variant of the invention in which ratio-values are computed from factory-site dry and wet calibration values and a relative characteristic is then derived from these ratio-values, differs from the above variants, from step a) iv. onwards, insofar as at the factory site ratio-values are computed from the factory-site wet calibration values and the factory-site dry calibration values; and from the ratio-values a relative characteristic of the sensors $S_0$ is obtained, which is taken to be valid for all sensors $S_n$ made in the same way; and at the user site a user-site ratio-value is computed from the user-site dry calibration value and the luminescence measurement value; and the concentration of the non-volatile analyte present in the aqueous sample is computed from the user-site ratio-value and the relative characteristic.

This variant of the invention also differs from the known procedures initially described in a number of points. Thus during factory-site calibration factory-site dry calibration values are obtained to which the factory-site wet calibration values are related by the computation of ratio-values. The relative characteristic is obtained from these factory-site ratio-values. At the user site a luminescence measurement is performed with the dry sensor, yielding a user-site dry calibration value to which the luminescence measurement value obtained from the sensor in contact with the sample is related by computing a user-site ratio-value. From the user-site ratio-value and the relative characteristic the concentration of the non-volatile analyte present in the aqueous sample is determined.

According to the invention an optical sensor for the determination of a non-volatile analyte may be used in combination or in a joint sensor configuration with sensors for the determination of the concentration of volatile analytes, such as $O_2$ or $CO_2$. Gas sensors and sensors for non-volatile analytes may for instance be combined in a single-use measuring element, e.g. in the form of a sensor array. The gas sensors are to be regarded as "calibration-free", if measurement is performed by means of luminescence decay time. With the help of a calibrating gas a single-point-calibration is also possible.

To facilitate understanding of the invention, wet calibration, though known in the art, is subsequently described in more detail for the case of an optical sensor with a PET dye. The following equations are immediately applicable to PET pH indicator dyes. For indicator dyes, based on the PET effect, for $Na^+$, $K^+$, $Ca^{++}$ see for instance U.S. Pat. Nos. 5,981,746 A, 6,211,359 B1 and 6,171,866 B1.

The given equations are also, with certain restrictions, applicable to ICT pH indicator dyes, specifically to such dyes where through suitable choice of spectral filters only one species may be excited or where the luminescence of only one species may be measured. The sign of the responses will change according to whether measured luminescence increases or decreases when the analyte is bound. In principle, the given equations are also applicable to ICT pH indicator dyes where through suitable choice of spectral filters none of the two species can be specifically excited nor their luminescence measured, for instance when the spectra overlap. The complexity of the mathematical expressions increases in this case.

Depending on the thermodynamic equilibrium constant $K_d$ of the indicator dye and on the concentration of the analyte S the indicator dye will have a species A to which the analyte S is not bound, and a species B to which the analyte S is bound.

The reversible binding is governed by the mass action law:

$$B \xrightleftharpoons{K_d} A + S \quad (1)$$

The dissociation constant $K_d$, which is dependent on the temperature and on the physical-chemical environment of the indicator dye, is given in a first approximation by equation 2, $$K_d = \frac{cA \cdot cS}{cB} \quad (2)$$

with C standing for concentration, and the index d meaning dissociation constant. $K_d$ is given in mol/l.

The ratio of the concentrations cA and cB is thus determined by the dissociation constant $K_d$ and the concentration of the analyte S.

$$\frac{cB}{cA} = \frac{cS}{K_d} \quad (3)$$

The $pK_d$-value (eqn. 4) is the negative logarithm to base 10 of the dissociation constant:

$$pK_d = -\log(K_d) \quad (4)$$

The concentration cD (total concentration) of the PET indicator is the sum of the concentrations of the individual indicator species A and B.

$$cD = cA + cB \quad (5)$$

The ratio of the concentration of the indicator species B to the total concentration of the indicator is $$V = cB/cD \quad (6)$$

If the species A is absent the ratio is 1. If the concentrations of the two species are equal the ratio is 0.5. If the species B is absent and only species A is present the ratio is 0.

For given excitation and emission wavelengths the luminescence intensity L of the PET indicator is the sum of the intensities $L_A$ and $L_B$ of the emitted light of the individual species A and B.

$$L = L_A + L_B \quad (7)$$

$L_A$ and $L_B$ are proportional to the concentrations CA and CB of the individual species A and B, where $L_A = k_A \cdot cA$ and $L_B = k_B \cdot cB$. The proportionality constants $k_A$ and $k_B$ are valid for a measurement system, that is for the combination of a sensor, from a set of sensors made in the same way, with a suitable measuring device.

For given excitation and emission wavelengths the proportionality constants $k_A$ and $k_B$ comprise α) sensor parameters, such as the total concentration cD of the dye, effective light pathlengths within the sensors, irradiated area, absorption values and luminescence quantum yield of the species A and B;

β) parameters of the individual measuring system, such as intensity of the light source, sensitivity of the detector and transmission values of the optical components.

PET indicators that are particularly suitable are characterized by the fact that $k_B$ preferably is larger by at least a factor 10, even more preferably by a factor 100, than kA, i.e. that the luminescence intensity of the species A—to which the analyte is not bound—is lower by this factor than the luminescence intensity of the species B—to which the analyte is bound. In the following it is assumed that $k_B > k_A$. Depending on the PET mechanism indicators could be found with $k_A > k_B$. As in the case of ICT indicators the expert would have to adapt the following equations accordingly.

Combining equations 2, 5 and 6 finally leads to an equation which describes the effective shape of the sensor characteristic:

$$L = L_m \left(1 + \frac{q - 1}{1 + \frac{cS}{K_d}}\right) \quad (8)$$

where $q = k_A/k_B$ and $L_m$ (m indicating maximum intensity) is the measured luminescence intensity, when only species B is present. $L_m$ may also be used as a scaling factor.

For given excitation and emission wavelengths and for a given measuring system equation 8 describes the measured (effective) luminescence intensity L as a function of the concentration of the analyte.

The following considerations apply to the parameter q:

The parameter q represents the ratio $k_A/k_B$ and thus the intensity of the pure species A versus the intensity of the pure species B, q.100 is the intensity of the pure species A as a percentage of the intensity of the pure species B.

The following considerations apply to the scaling factor $L_m$:

For a given measuring system $L_{mA}$ is the lowest measurable intensity of a sensor. A sensor may for instance be set to lowest intensity by bringing it into contact with a measurement medium whose concentration of analyte S is very small compared with $K_d$ ($cS \ll K_d$), which means that the equilibrium (see eqn. 1) is completely shifted to the left side. Typically it will be sufficient if cS is smaller than $K_d$ by a factor $10^3$ to $10^4$.

For a given measuring system $L_{mB}$ is the highest (maximum) intensity of a sensor (which can be achieved with the analyte in question). A sensor may for instance be set to maximum intensity by bringing it into contact with a measurement medium whose concentration of analyte S is very high compared with $K_d$ ($cS \gg K_d$), which means that the equilibrium (see eqn. 1) is completely shifted to the right side. Typically it will be sufficient if cS is greater than $K_d$ by at least a factor $10^3$ to $10^4$.

In equation 8 $L_m$ is to be taken as $L_{mB}$, i.e. the maximum intensity of the sensor.

In the case of particularly efficient PET dyes q may tend to zero. Such dyes are particularly suitable since their species A is not luminescent and its dry luminescence therefore need not be taken into account. In the case of ICT dyes, where only one species, e.g. B, is measured by using suitable spectral filters (see description above) q is zero (since luminescence of A is not measured, whether it be luminescent or not). Since q is equal to zero, eqn. 8 reads $L = L_m(1 - 1/(1 + cS/K_d))$. If species A is measured instead of species B, eqn. 8 reads $L = L_m(1 - 1/(1 + K_d/cS))$. The other equations must be changed accordingly.

If equation 8 is divided by a constant (>0), for instance by $L_m$, there results a relative characteristic $L_{rel}$, referenced to the value of the constant.

$$L_{rel} = 1 \cdot \left(1 + \frac{q-1}{1 + \frac{cS}{K_d}}\right) \quad (9)$$

$L_{rel}$ in eqn. 9 can assume values between q and 1.

The parameters $K_d$ and q determine the shape of the characteristic which is independent of the scaling factor $L_m$. These parameters are independent of the quantities cited above in paragraphs α) and β), and can be determined by factory-site calibration. The parameter $L_m$ takes into account the quantities cited above in paragraphs α) and β).

By multiplying the relative characteristic $L_{rel}$ (which can be determined by factory-site calibration with a factory-site measuring system) with the parameter $L_m$ (which can be determined with a user-site measuring system) the characteristic valid for the user-site measuring system (effective characteristic) is obtained.

If the scaling factor $L_m$ refers to a sensor in the wet state (wet sensor), it will be designated by the index W ($L_{mW}$) in the following. If it refers to a sensor in the dry state (dry sensor) it will be designated by the index D ($L_{mD}$).

The scaling factor $L_{mW}$ is identical with the maximum luminescence intensity which can be measured with a given wet sensor in a given measuring system. $L_{mW}$ is directly measurable in a wet calibration with a calibrating medium, provided that the analyte concentration is chosen such that only species B is present.

In the case of pH sensors eqn. 8 may also be written in the form of eqn. 10 with pH=−log(aH⁺) and pK=−log($K_d$).

$$L = L_{mW}\left(1 + \frac{q-1}{1 - 10^{pH-pK}}\right) \quad (10)$$

In the following the superscript * is used for all quantities which refer to the factory site (factory-site calibration).

The parameters q and $K_d$, are, for instance, determined by the following steps:
a) Selection of at least one sensor from a plurality of sensors made in the same way;
b) Factory-site measurement with the selected sensor of the luminescence intensities $L_{iW}$* with a number n (where n is at least 3, preferably 5 or greater, if eqn. 8 or 10 is applied) of aqueous calibration media with known concentrations $cS_i$* of the analyte, which are distributed at least over the expected range of the measurement variable, yielding n data pairs ($cS_i$*, $L_{iW}$*; i=1 . . . n);
c) Fitting of a suitable mathematical equation describing the sensor characteristic (e.g. eqn. 8 or 10) to the n data pairs, for instance by known least square methods, resulting in values for the parameters q, $K_d$ and $L_{mW}$*.

The parameter $L_{mW}$* found at the factory site depends on the measuring device used at the factory site and is irrelevant for user-site measurement.

It is of particular advantage if the parameters q and $K_d$ are determined not with a single sensor but with a representative number of sensors. By averaging the values q and $K_d$ of individual sensors, mean values of these parameters are obtained, which may be assigned to the plurality of sensors made in the same way.

Thus it is possible to determine by factory-site calibration the relative characteristic (in the form of the parameters q and $K_d$ or pK) and to supply it together with the sensor to the user, for instance in bar-code form. If a sensor from a set of sensors made in the same way is then inserted into a user-site measuring device, $L_{mW}$ is at first unknown. It could for instance be measured directly in an aqueous single-point-calibration. All parameters describing the effective characteristic would then be known.

If the calibrating medium is replaced by the sample in actual measurement and the luminescence intensity L is measured in contact with the sample, the analyte concentration can be deduced from equations 8 or 10 by solving for cS or pH.

If equation 8 is solved for cS (setting $L_m = L_{mW}$), one gets:

$$cS = K_d((q-1)/(L/L_{mW}-1)-1) \quad (11)$$

Since the analyte concentration necessary in the calibration medium for direct determination of $L_{mW}$, lies beyond the measurement range of interest, it is often undesirable to determine $L_{mW}$ directly.

It is advantageous to perform the single-point-calibration at an analyte concentration which lies in the expected range of the sample analyte concentration. Preferably the analyte concentration is chosen such that the ratio cB/cD (eqn. 6) has a value between 0.1 and 0.9, even more preferably between 0.3 and 0.7.

With the intensity value $L_{cal}$, measured at the user site during single-point-calibration with the wet sensor in contact with a calibration medium of known analyte concentration $cS_{cal}$, and the parameter values q and $K_d$ known from factory calibration, $L_{mW}$ is computed from eqn. 12:

$$L_{mW} = L_{cal} \bigg/ \left(1 + \frac{q-1}{1 + \frac{cS_{cal}}{K_d}}\right) \quad (12)$$

The disadvantages of the procedure described above for the conventional calibration of optical sensors with an indicator dye, stem from the fact that, despite the majority of calibration steps having been performed at the factory, at least a single-point-calibration (with an aqueous calibration medium) must still be performed at the user site prior to the actual measurement. This requires the acquisition and management of an aqueous calibration medium (handling, storage, distribution, re-ordering, checking of expiry dates etc.). This disadvantage is overcome by the method of the present invention in which at the user site only dry calibration steps are carried out, but no wet calibration steps.

DESCRIPTION OF THE DRAWINGS

In the following the invention will be described in more detail with the aid of diagrams and schematic drawings.

DETAILED DESCRIPTION

EXAMPLE 1

(With Sub-Variants 1.1 (FIG. 1a), 1.2 (FIG. 1b), and 1.3 (FIG. 1c) Using Equations 1 to 10)

Figure 1A:
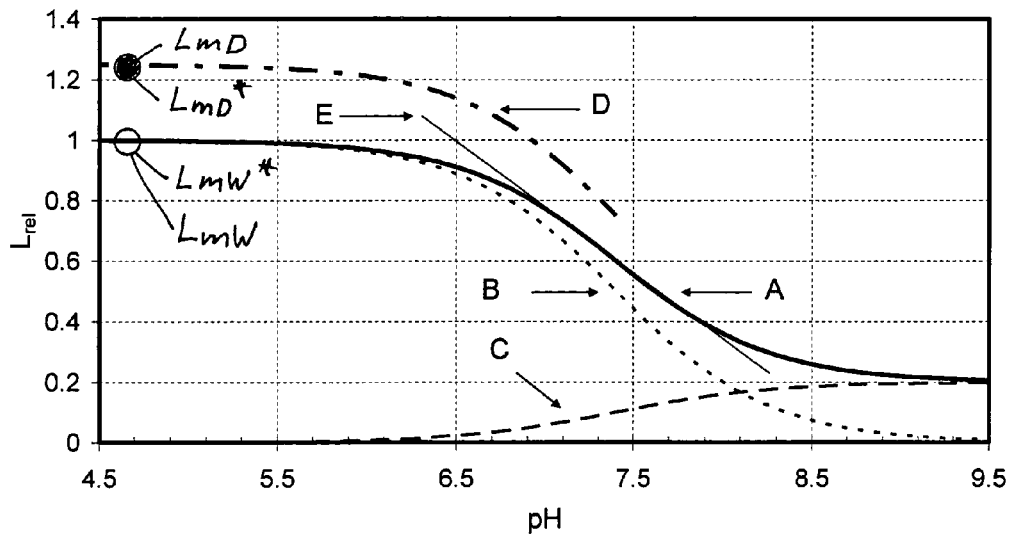
FIGS. 1a to 1c show the luminescence intensities scaled to $L_{mW}=1$ of the individual species of a pH sensor as functions of the pH-value (in the pH range 4.5 to 9.5) for different subvariants of the procedure according to the invention.
Figure 1B:
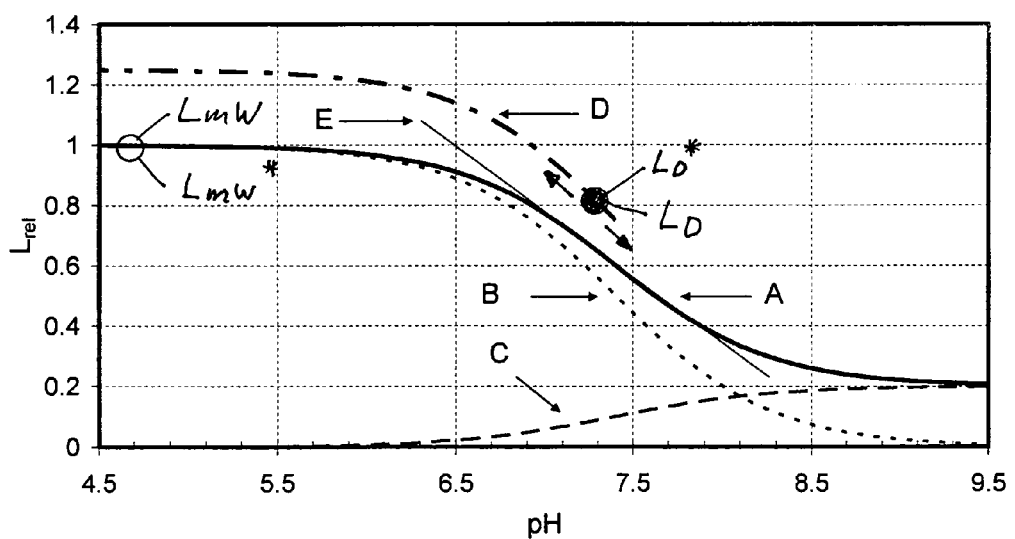
Figure 1C:
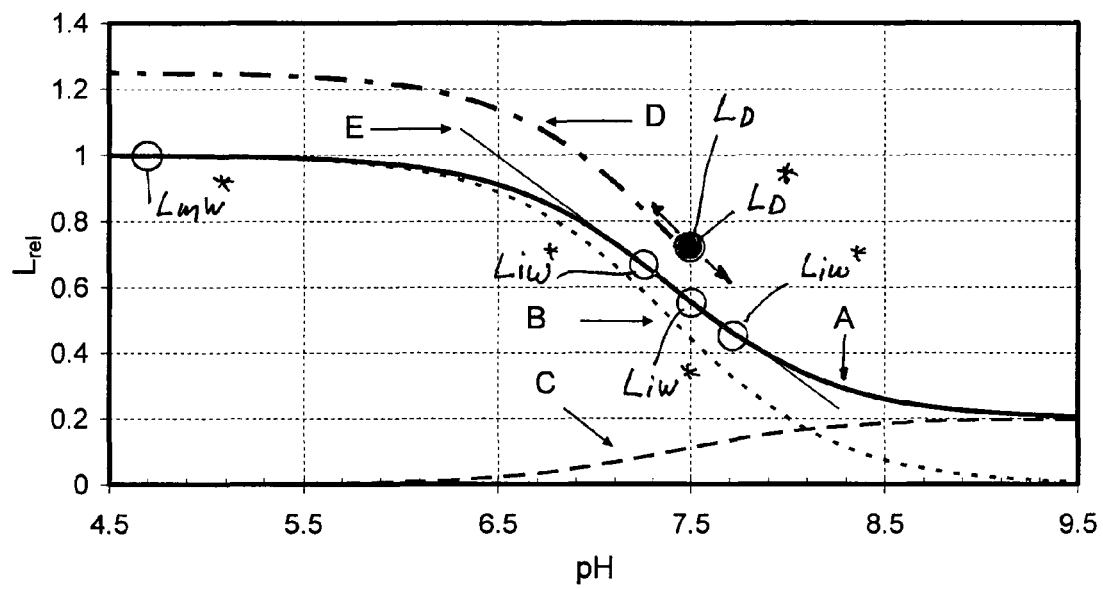

In FIGS. 1a to 1c, which illustrate the sub-variants 1.1, 1.2 and 1.3 described in the following, the luminescence intensities scaled to $L_{mW}=1$ of the individual species of a pH sensor (i.e., with H$^+$ being the non-volatile analyte) are shown as functions of pH-value. Curve A represents the relative characteristic and is the sum of the luminescence intensities $L_{AW}$ and $L_{BW}$ of the individual species A and B. It was obtained from equation 10, with the value 7.4 used for parameter pK and the value 0.2 used for the parameter q, and equation 10 divided by $L_{mW}$. The ratio between lowest intensity (right side) and highest intensity (left side) is the value of the parameter q. Curve B is the relative luminescence intensity of species B as a function of pH-value. Curve C is the relative luminescence intensity of species A as a function of pH-value. From curves B and C it can be seen that for pH<4.5 essentially only species B is present, while for pH>9.5 essentially only species A is present. Curve D is the sum of the luminescence intensities $L_{AD}$ and $L_{BD}$ of the individual species A and B in the dry sensor as functions of pH-value during manufacture of the sensors. For the illustration it was assumed that the luminescence intensity of species B in the dry state is greater by a factor 1.25 than in the wet state. Depending on the dye and on the matrix it could also be equal or smaller. Towards higher pH-values the intensity of dry luminescence decreases with a decrease in the concentration of the stronger luminescent species B whereas the concentration of the lesser luminescent species A increases. From curve E it can be seen that within a limited pH range (approx. pH 7.0-7.8) the relative characteristic may be represented by a straight line of the general form $L_W=a+b \cdot pH$. Outside of this range the characteristic cannot be approximated by the linear function with sufficient accuracy. The measurement values designated by * in the individual figures are factory-site values, the values without * pertain to the user site.

Figure 2:
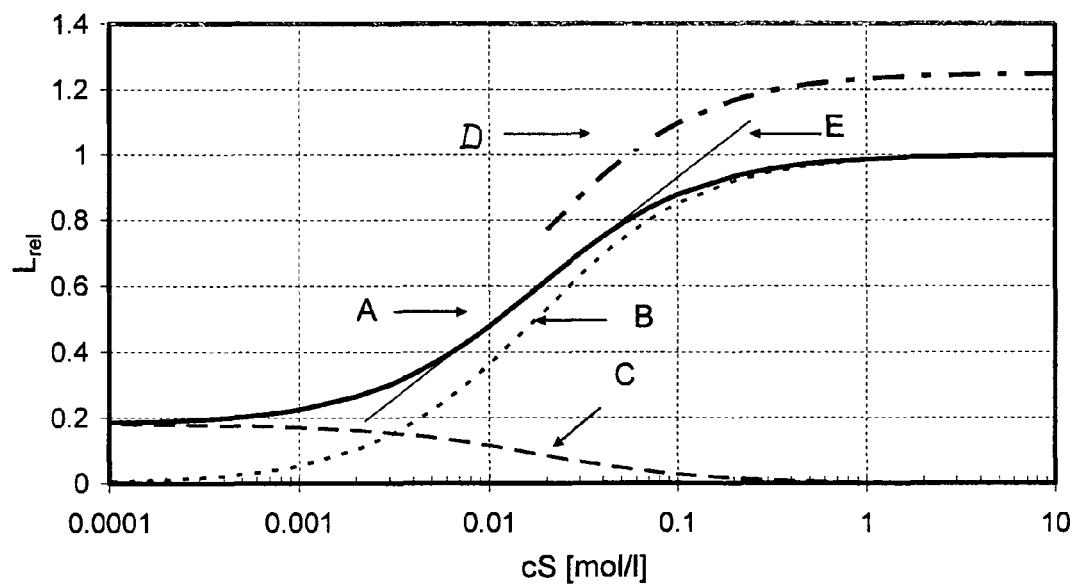
FIG. 2 shows the luminescence intensities scaled to $L_{mW}=1$ of the individual species of an ion sensor as functions of ion concentration in mol/l with the abscissa logarithmically scaled.

FIG. 2 illustrates the luminescence intensities scaled to $L_{mW}=1$ of the individual species of an ion sensor as functions of ion concentration. The abscissa is logarithmically scaled. Curves A to D are analogous to those of FIGS. 1a to 1c. Curve A was obtained from eqn. 8 with the value 0.0176 for parameter $K_d$ and the value 0.18 for parameter q and eqn. 8 divided by $L_{mW}$. The values have been taken from table 1 of U.S. Pat. No. 6,211,359. Eqn. 8 essentially corresponds to eqn. 6 of U.S. Pat. No. 6,211,359 with the difference that eqn. 8 does not take into account interfering ions in order to keep the presentation simple. Eqn. 8 also corresponds to eqn. 4 of U.S. Pat. No. 6,171,866 with the difference that there the presentation is logarithmic. From curve E it can be seen that within a limited range of concentrations (cS=0.006-0.05 mol/l approx.) the relative characteristic may be represented by a straight line of the general form $L_W=a+b \cdot \log(cS)$. Outside of this range the characteristic cannot be approximated by the linear function with sufficient accuracy.

Due to the definition of $L_m$ (m indicating maximum intensity, i.e. the intensity when essentially only species B is present) a special case is described in example 1.1 following below, examples 1.2 and 1.3 dealing with the general case.

EXAMPLE 1.1 (FIG. 1a)

Surprisingly it has been found that for sensors made in the same way and measured with devices of the same type, the ratio $$R_{mD/W}=L_{mD}/L_{mW}=L_{mD}{}^*/L_{mW}{}^* \tag{13}$$

is constant and can be determined by factory-site calibration. Thus the scaling factor $L_{mW}$ may be determined from $L_{mD}/R_{mD/W}$. At the user site therefore only a single-point-dry-calibration will be necessary for determination of the scaling factor $L_{mW}$ and no calibrating medium will be required. This means that a true dry calibration of a luminescence-optical sensor is obtained at the user site, such that liquid calibration media for single-point-calibration may be altogether dispensed with.

$L_{mD}{}^*$, respectively $L_{mD}$, are the maximum intensity values measured with dry sensors at the factory site, respectively at the user site. These values can be determined if the indicator dye of the sensor is set up in such a way that in the dry state the whole mass of the indicator is present in the form of species B, i.e. the luminescent indicator dye is present essentially completely as the species B with the ratio V=cB/cD (eqn. 6) equal to 1, since cD=cA+cB (eqn. 5).

$L_{mW}{}^*$, respectively $L_{mW}$, are the maximum intensity values measured at the factory site, respectively at the user site, with wet sensors. The value $L_{mW}{}^*$ can be measured at the factory site with the sensor in contact with a liquid calibrating medium and with the analyte concentration of the calibrating medium adjusted in such a way that after wet-up and with equilibrium reached (eqn. 1 resp. 2) essentially only species B is present, the ratio V=cB/cD (eqn. 6) in the wet sensor being equal to 1. $L_{mW}$ may then be computed from eqn. 13.

A variant of the method of the invention for an optical sensor with an indicator dye, which can be present as a species A—free of the analyte S—or as a species B—to which the analyte S is bound—, and whose characteristic is given by eqn. 8 or eqn. 10, is characterized by the fact that during factory calibration when the indicator dye is essentially completely present in the form of species B, a ratio-value $R_{mD/W}$ (from an intensity value $L_{mD}{}^*$ without aqueous calibration medium, and an intensity value $L_{mW}{}^*$ with aqueous calibration medium) is computed, such that eqn. 8 becomes, with $L_{mW}=L_{mD}/R_{mD/W}$, $$L = \frac{L_{mD}}{R_{mD/W}}\left(1 + \frac{q-1}{1+\frac{cS}{K_D}}\right) \tag{14}$$

and that $L_{mD}$ may be determined in a subsequent user-site single-point dry calibration, i.e. without the use of an aqueous calibrating medium.

If the sensors are manufactured in such a way that in the dry state only species B is present, the intensity measured in the dry state will be $L_{mD}$. Following wet-up and equilibration at the factory site with a liquid calibrating medium whose analyte concentration is chosen such that only species B is present, $R_{mD/W}$ may be determined directly from eqn. 13.

The first subvariant according to the invention (FIG. 1a) is thus characterized in that:

in step a)i.
    sensors $S_0$ are selected, in which the luminescent indicator dye is essentially completely present as a species B, to which the analyte or an analogue of the analyte is bound, in step a) ii.
    factory-site dry calibration values $L_{mD}^*$ are obtained, in step a)iii.
    for at least one of the aqueous calibrating media the concentration of the analyte S is chosen such that after wet-up and equilibration essentially only the species B is present and factory-site wet calibration values $L_{mW}^*$ are measured, in step a)iv.
    from the factory-site dry calibration values $L_{mD}^*$ and the factory-site wet calibration values $L_{mW}^*$ a ratio-value $R_{mD/W}$ is computed, in step b)i.
    a user-site dry calibration value $L_{mD}$ is obtained, and in step b)iii.
    a user-site scaling factor $L_{mW}$ is computed from $L_{mD}$ and the ratio-value $R_{mD/W}$, and the concentration of the non-volatile analyte is determined from the measured luminescence value, the user-site scaling factor $L_{mW}$ and the relative characteristic.

EXAMPLE 1.2 (FIG. 1b)

In example 1.1 the ratio V of the concentration of species B—to which the analyte S is bound—to the total concentration D of the indicator is 1. In other words: in the dry state the indicator dye is completely present in the form of species B.

Typically optical sensors are manufactured in such a way that in the dry state the ratio V=cB/cD has a value between 0.1 and 0.9 and preferably lies between 0.3 and 0.7. For each value of the ratio V there exists a value $R_{D/W}$ which may be used to deduce the maximum wet luminescence intensity $L_{mW}$ from the intensity $L_D$ measured in the dry state. If—as illustrated in example 1.1—cA tends to zero, essentially only species B is present and the equality $R_{D/W}=R_{mD/W}$ holds.

In modification of eqn. 13 one obtains from eqn. 15

$$R_{D/W}=L_D/L_{mW}=L_D^*/L_{mW}^* \quad (15)$$

a ratio $R_{D/W}$ by which the relative characteristic can be related to the user-site dry calibration value.

The second subvariant according to the invention (see FIG. 1b) is thus characterized in that:

in step a)i.
    sensors $S_0$ are selected, in which the indicator dye is present in the form of a species A and a species B, the analyte or an analogue thereof binding to the species B and not binding to species A, the ratio V=cB/cD, with cD=cA+cB, being known and lying between 0.1 and 0.9, preferably between 0.3 and 0.7, in step a)ii.
    dry factory calibration values $L_D^*$ are obtained, in step a)iii.
    for at least one of the aqueous calibrating media the concentration of the analyte S is chosen such that after wet-up and equilibration essentially only the species B is present and factory-site wet calibration values $L_{mW}^*$ are measured, and in step a)iv.
    from the factory-site dry calibration values $L_D^*$ and the factory-site wet calibration values $L_{mW}^*$ a ratio-value $R_{D/W}$ is computed, in step b)i.
    a user-site dry calibration value $L_D$ is obtained, and in step b)iii.
    a user-site scaling factor $L_{mW}$ is computed from $L_D$ and the ratio-value $R_{D/W}$, and the concentration of the non-volatile analyte is determined from the luminescence measurement value, the user-site scaling factor $L_{mW}$ and the relative characteristic.

EXAMPLE 1.3 (FIG. 1c)

In the examples 1.1 and 1.2 described above, the concentration of the analyte S for measuring the wet factory calibration value $L_{mW}^*$ must be chosen such that essentially only species B of the indicator is present.

In practice it is frequently undesirable and in the case of some sensors or analytes outright disadvantageous or impossible, to set the analyte concentration in a calibrating medium in such a way that after wet-up and equilibration (eqn. 1 or 2) essentially only species B is present, permitting direct measurement of $L_{mW}^*$ (see above under a.iii). The reason for this is that—in order to shift equilibrium completely to the left in eqn. 1—very high analyte concentrations (>1 mol/l) would have to be achieved in some cases.

A $Na^+$ sensor for measuring physiological $Na^+$ concentrations ideally has a $K_d$ value of roughly 0.150 mol/l, for instance. To shift the equilibrium (in eqn. 1 and 2) to the left side, such that essentially only species B is present, the analyte concentration would have to be higher than the $K_d$ value by a factor 100, ideally by a factor 1000. A resulting analyte concentration in the calibrating medium of 15 mol/l or higher is neither practical nor possible, due to solubility limitations.

As a further example take a pH sensor (with $H^+$ as the non-volatile analyte) for determination of physiological pH values, which ideally has a $K_d$ of about $3.4*10^{-8}$ (corresponding to a pK value of 7.4). To shift the equilibrium (in eqn. 1 and 2) to the left side, such that essentially only species B is present, the analyte concentration must be higher than the $K_d$ value by a factor 100, ideally by a factor 1000. Setting the analyte concentration ($cH^+$) in the calibration medium at $3.4*10^{-8}$ or higher, corresponding to a pH of 4.4 or lower, presents no problem, but may be undesirable if weakly or strongly acidic calibration media are to be avoided for some reason.

When the parameter values q and $K_d$ are known (obtained from the factory-site calibration) the concentration $cS_i$ of the analyte in the liquid calibration medium may be chosen such in procedure step a)iii of factory calibration that (after wet-up) a known ratio V=cB/cD is established in the wet sensor, which preferably lies in the range between 0.1 and 0.9, in particular between 0.3 and 0.7. It is of particular advantage if this wet-state ratio (procedure step c) is chosen such that it equals the dry-state ratio (procedure step b).

This variant will then yield the wet calibration value $L_{iW}^*$. Using eqn. 12 $L_{mW}^*$ may for instance be computed from $L_{iW}^*$.

$$L_{mW}^* = L_{iW}^* (1+(q-1)(1+cS_i/K_d)) \quad (16)$$

The third subvariant according to the invention (see FIG. 1c) is thus characterized in that:

in step a)i.
    sensors $S_0$ are selected, in which the indicator dye is present in the form of a species A and a species B, the analyte or an analogue thereof binding to the species B and not binding to species A, the ratio of the concentrations of the species V=cB/cD, with cD=cA+cB, being known and lying between 0.1 and 0.9, preferably between 0.3 and 0.7, in step a)ii.
factory-site dry calibration values $L_D^*$ are obtained, in step a)iii.
luminescence intensity is measured with the sensors $S_0$ for at least two aqueous calibrating media with known, different concentrations $cS_i$ of the analyte S yielding at least two factory-site wet calibration values $L_{iW}^*$, and in step a)iv.
the relative characteristics and the wet calibration values $L_{mW}^*$ of the sensors $S_0$ are obtained from the value pairs $L_{iW}^*$, $cS_i$ and the relative characteristic valid for all sensors $S_n$ made in the same way is computed therefrom, in step a)iv.
from the dry calibration values $L_D^*$ and the wet calibration values $L_{mW}^*$ a ratio-value $R_{D/W}$ is computed, yielding in step b)i.
a user-site dry calibration value $L_D$, and in step b)iii.
a user-site scaling factor $L_{mW}$ is computed from $L_D$ and the ratio-value $R_{D/W}$, and the concentration of the non-volatile analyte is determined from the luminescence measurement value, the dry calibration value $L_D$, the ratio-value $R_{D/W}$ and the relative characteristic.

EXAMPLE 2

(With Subvariants 2.1 and 2.2 Not Using Equations 1 to 10)

It is an advantage of theoretically derived functional equations for the sensor characteristic that they usually describe the shape of the characteristic curve over the whole range of measurable analyte concentrations with sufficient accuracy. But for the purpose of dry calibration according to the invention it is not absolutely necessary to use the above, theoretically derived equations.

In principle alternative functional relationships may be used. The shape of the characteristic curve—at least over the expected range of the analyte concentration—can be represented sufficiently accurately, for instance by polynomials of first or second degree, by logarithmic functions, by rational functions or by combinations of these functions (e.g. $L_W=a+b \cdot cS$, $L_W=a+b \cdot \log(cS)$, $L_W=a+b \cdot cS+c \cdot (cS)^2$, or $L_W=a+b \cdot pH$, $L_W=a+b \cdot \log(pH)$, $L_W=a+b \cdot pH+c \cdot (pH)^2$). The functions cited as examples differ from the theoretically derived functions (e.g. eqn. 8 or 10) for instance insofar as their parameter sets (a, b, c) do not contain a specific parameter which could be used as a scaling factor analogous to $L_m$, and further as the individual parameters, in contrast to q and $K_d$ of eqn. 8, do not reflect specific properties of the sensor. If such alternative functions are used and the analyte concentration unexpectedly lies outside the assumed range, there is a risk that the values of the characteristic do not correlate closely enough with the measurement values, thus leading to false results. If the function does not approximate the shape of the characteristic closely enough over the expected range of analyte concentrations, the results will be imprecise.

Alternative functions could for instance be used, if
theoretically derived functions are not available or are not known with sufficient accuracy;
the dynamic range of the sensor is larger than the expected range of analyte concentrations and the alternative function represents the shape of the characteristic in the expected range with sufficient accuracy.

There are two different approaches which, while differing formally and in details of procedure, are basically equivalent:
normalizing the characteristic obtained by factory-site calibration by the dry value (see example 2.1),
normalizing the measured points obtained by factory-site calibration by the dry value (see example 2.2).

A given ratio $V_D$ (eqn. 6) of the indicator species A and B present in a dry sensor $S_0$ will in dry measurement result in an intensity $L_D$.

$L_D$ is the luminescence intensity measured with the dry sensor, at a given ratio $V_D$, the ratio between the concentrations of the two indicator species A and B being the same for every dry sensor from a plurality of sensors $S_n$ made in the same way.

In contact with a liquid medium, i.e. a calibrating or controlling medium or the sample containing the analyte S to be measured in the concentration $cS_i$, a new ratio $V_{iW}$ of the species A and B is established after wet-up and equilibration in the wet sensor, where the ratio $V_{iW}$ established in the wet sensor depends on the concentration $cS_i$ of the analyte in the sample and the dissociation constant $K_d$ of the indicator, and a luminescence intensity $L_{iW}$ corresponding to the ratio $V_{iW}$ is measured.

$L_{iW}$ thus is the luminescence intensity measured with the wet sensor in contact with a sample containing the analyte S in a concentration cSi to be determined.

And thus—with the ratio $V_D$ given—each ratio-value $L_{iW}/L_D$ corresponds to a certain concentration of the analyte in the sample.

The ratio-values $L_{iW}/L_D$ are essentially independent of the influencing factors cited above under $\alpha$) and $\beta$). To determine these ratio-values the intensities $L_{iW}$ and $L_D$ must be measured with one and the same sensor and with the same measuring device.

For a given value $V_D$ in the dry sensor there is a certain functional relationship between the ratio-values $L_{iW}/L_D$ and the concentration of the analyte in the sample.

EXAMPLE 2.1

In a preferred variant of the method according to the invention a representative number of dry sensors $S_0$ is selected from a plurality of sensors $S_n$ made in the same way and the luminescence intensity $L_D^*$ is measured without the use of an aqueous calibrating medium. Subsequently each of the sensors $S_0$ is brought into contact with a number n of aqueous calibrating media with known concentrations cSi of the analyte, which are distributed at least over the expected range of the concentration to be measured, and n luminescence intensities ($L_{iW}^*$; i=1 ... n) are measured, yielding n data pairs ($cS_{iW}^*$, $L_{iW}^*$; i=1 ... n).

A suitable function of general form $L_W^*=f(P_1^*, \ldots, P_n^*, cS \text{ or } pH)$ (e.g. $L_W^*=P_1^*+P_2^* \cdot cS$ or $L_W^*=P_1^*+P_2^* \cdot pH$) describing the shape of the sensor characteristic is fitted to the n data pairs, resulting—at least for part of the range of the analyte concentrations to be measured—in values for the parameters $P_1^*, \ldots, P_n^*$ of an effective sensor characteristic obtained at the factory site.

From the effective characteristic obtained at the factory site the relative characteristic is derived by scaling with the dry value $L_D^*$, that is the characteristic is divided by the dry value $L_D^*$.

For example: the effective factory-site characteristic $L_W^*=P_1^*+P_2^* \cdot cS$ is divided by $L_D^*$, i.e. the ratios $p_1=P_1^*/$ $L_D^*$ and $p_2 = P_2^*/L_D^*$ are computed and the scaled characteristic is $L_{rel} = (P_1^* + P_2^* \cdot cS)/L_D^* = (p_1 + p_2 \cdot cS)$.

At the user site a single-point-dry-calibration (no aqueous calibrating medium is used) is performed using a dry sensor $S_1$ from the plurality of sensors made in the same way, yielding a luminescence intensity $L_D$.

Multiplying the relative characteristic $L_{rel}$ with the dry calibration value $L_D$ measured at the user site gives the effective characteristic valid for the user site.

Continuing the above example: the relative characteristic $L_{rel} = (p_1 + p_2 \cdot cS)$ is multiplied with the user-site dry calibration value $L_D$. I.e., the parameters $p_1$ and $p_2$ of the relative characteristic are multiplied with the dry calibration value $L_D$ measured at the user site: $P_1 = L_D \cdot p_1$ and $P_2 = L_D \cdot p_2$; and the effective characteristic at the user site is $L_W = L_D \cdot (p_1 + p_2 \cdot cS) = (L_D \cdot p_1 + L_D \cdot p_2 \cdot cS) = (P_1 + P_2 \cdot cS)$. Thus the user-site relative characteristic is referenced to the dry calibration value.

From the user-site effective characteristic the analyte concentration is obtained by solving the equation for cS (or pH) and entering the value $L_{iW}$ of the luminescence intensity measured in contact with the sample. In the present example: $cS_i = (L_{iW} - P_1)/P_2$.

In order to be able to obtain reliable mean values of the parameters $p_1$ to $p_n$ of the characteristic the expert may select a representative number m of sensors. Theoretically m=1 is possible, but in practice m will be a larger number, depending on the given application, m will be >16, preferably ≧40.

In an advantageous subvariant of the second variant it is provided that at least m sensors are selected and m dry calibration values $L_D^*$ are obtained at the factory site and that following the dry measurement wet calibration values $L_{iW}^*$ are obtained from each sensor using at least two of n≧2 different aqueous calibration media, with each calibration medium being used at least once during the calibration of all of the selected sensors. For each sensor an effective characteristic of general form $L_W^* = f(P_1^*, \ldots, P_n^*, cS \text{ or } pH)$ is derived from the at least two of n≧2 wet calibration values $L_{iW}^*$, and for each sensor a relative characteristic of general form $L_{rel} = f(p_1, \ldots, p_n, cS \text{ or } pH)$ is computed by dividing the effective characteristic by the dry calibration value $L_D^*$. Subsequently a relative characteristic is obtained by averaging the coefficients $p_1$ to $p_n$ of the individual sensor characteristics, and this relative characteristic is assigned to the totality of all sensors $S_n$ made in the same way, i.e. a production lot of sensors.

A subvariant of the second variant of the invention is thus characterized as follows:

at the factory site at least m sensors $S_0$ are selected from a plurality of sensors made in the same way;

the luminescence intensity is measured for each selected sensor $S_0$ without aqueous calibration medium, giving a factory-site dry calibration value $L_D^*$ for each sensor;

for each selected sensor the luminescence intensities are measured when in contact with at least 2 of n (n≧2) different, aqueous calibrating media, each calibration medium being used at least once in the calibration of all of the selected sensors, yielding at least two factory-site wet calibration values $L_{iW}^*$ for each sensor;

for each selected sensor a suitable function of general form $L_W^* = f(P_1^*, \ldots, P_n^*, cS \text{ or } pH)$ describing the shape of the sensor characteristic is fitted to the data pairs ($cS_i^*$, $L_{iW}^*$), resulting for each sensor in values for the parameters $P_1^*, \ldots, P_n^*$ of an effective factory-site characteristic;

for each selected sensor the effective factory-site characteristic is scaled with the corresponding factory-site dry calibration value $L_D^*$, resulting in parameters $p_1$ to $p_n$ for the relative characteristic of general form $L_{rel} = f(p_1, \ldots, p_n, cS \text{ or } pH)$ of the individual sensors;

by averaging the coefficients of the individual sensor characteristics a relative characteristic is obtained which is assigned to the totality of all sensors $S_n$ made in the same way.

at the user site for a sensor $S_1$ from the plurality of sensors $S_n$ made in the same way luminescence intensity is measured yielding a user-site dry calibration value $L_D$;

for the sensor $S_1$ in contact with the aqueous sample medium the luminescence intensity $L_{iW}$ is measured;

the relative characteristic obtained at the factory-site is scaled with the user-site dry calibration value $L_D$ resulting in values for the parameters $P_1$ to $P_n$ for the effective characteristic at the user site, which has the general form $L_W = f(P_1, \ldots, P_n, cS \text{ or } pH)$;

the analyte concentration is computed by solving the equation of general form $L_W = f(P_1, \ldots, P_n, cS \text{ or } pH)$ for cS or pH (cS or pH=$f(P_1, \ldots, P_n, L_W)$) and entering the user-site luminescence measurement value $L_{iW}$.

EXAMPLE 2.2

In a particularly preferred variant of the invention the following variation of the procedure outlined under example 2.1 also is possible. First ratio-values are computed from the factory-site wet calibration values $L_{iW}^*$ with a number n of calibrating fluids and the factory-site dry calibration value $L_D^*$, and the functional relationship between these ratios of wet values against dry value and the analyte concentrations or pH-values is expressed in the form of a table or a suitable function of the general form $L_{rel} = f(u_1, \ldots, u_n, cS \text{ or } pH)$.

In this variant of the method according to the invention at least one dry sensor $S_0$ is selected from a plurality of sensors made in the same way and the luminescence intensity $L_D^*$ is measured without an aqueous calibrating medium. Subsequently the sensor is brought into contact with a number n of aqueous calibrating media with known concentrations cSi of the analyte, distributed at least over the expected range of the concentration to be measured, and n luminescence intensities ($L_{iW}^*$; i=1 ... n) are measured, yielding n data pairs ($cS_{iW}^*$, $L_{iW}^*$; i=1 ... n).

For each of the selected sensors $S_0$ the measured luminescence intensities $L_{iW}^*$ are divided by $L_D^*$, giving the ratio-values $U_i^* = L_{iW}^*/L_D^*$; i=1, ..., n and thus n data pairs ($cS_i^*$, $U_i^*$; i=1, ..., n)

Then a suitable function of the general form $L_{rel} = f(u_1, \ldots, u_n, cS \text{ or } pH)$ describing the relative characteristic of the sensor (e.g. $L_{rel} = u_1 + u_2 \cdot cS$ or $L_{rel} = u_1 + u_2 \cdot pH$) is fitted to the data pairs obtained, resulting in values for the parameters $u_i$ to $u_n$ of the relative characteristic.

At the user site a single-point-dry-calibration (without an aqueous calibrating medium) is performed using a dry sensor $S_n$, giving a luminescence intensity $L_D$ which is the user-site dry calibration value; then the sensor is brought into contact with the sample containing the analyte S with (unknown) concentration $cS_i$ and a wet measurement, i.e. a measurement where the sensor is in contact with the aqueous sample is performed, yielding the luminescence intensity $L_{iW}$, i.e. the luminescence measurement value.

From the sample intensity value $L_{iW}$ and the dry intensity value $L_D$ a ratio $U_i=L_{iW}/L_D$ is computed. Using the sample intensity value $U_i$ referenced to the dry intensity value and the characteristic of the general form $L_{rel}=f(u_1, \ldots, u_n, cS$ or $pH)$ also referenced to the dry value, the analyte concentration or the pH value is deduced by solving for cS or pH.

The essential difference between the present variant and that described in example 2.1 is the following: in 2.1 the effective factory characteristic of general form $L_W^*=f(P_1^*, \ldots, P_n^*, cS$ or $pH)$ is obtained by measuring n calibrating values with n aqueous calibrating media, computing the parameters $P_1^*$ to $P_n^*$ and deriving the relative characteristic of the general form $L_{rel}=f(p_1, \ldots, p_n, cS$ or $pH)$ by scaling the effective characteristic with the dry value measured at the factory site, while in 2.2 the individual n wet calibration values are first scaled with the dry value measured at the factory site (that is, the n wet calibration values are divided by the dry value $L_D^*$ to obtain n ratio values) and then a relative characteristic is derived by fitting the n ratio values to the relative characteristic of the general form $L_{rel}=f(u_1, \ldots, u_n, cS$ or $pH)$.

In an advantageous further embodiment of the invention it is proposed that at least m sensors are selected at the factory site and that m dry calibration values $t_i$, with i=1 to m, are obtained, and that from each sensor wet calibration values with at least one of $n \geqq 2$ different aqueous calibration media are taken, each calibration medium being used at least once, such that $k \geqq n$ wet calibration values $k_{ij}$, with j=1 to n, are obtained, and that ratio-values $k_{ij}/t_i$ are computed from the individual pairs $t_i$, $k_{ij}$ and that the relative characteristic of the sensor is derived from these ratio-values.

The number of selected sensors is m (m may be 1, typically is >1, and in practice is a larger number, such as $\geqq 16$, and preferably $\geqq 40$, depending on the application, in order to get representative mean values), with the index i of the selected sensors running from 1 to m. There will thus be m dry calibration values $t_i$ with i=1 to m. The number of different, aqueous calibration media is $n \geqq 2$, with the index j of the aqueous calibration media running from j=1 to n. There are thus $k \geqq n$ wet calibration values $k_{ij}$ and k ratio-values $k_{ij}/t_i$.

The table below lists the values for 2, 3 and 5 calibration media:

A subvariant of this variant of the invention is thus characterized as follows:

at the factory site
    at least m sensors $S_0$ are selected from a plurality of sensors made in the same way;
    for each selected sensor the luminescence intensity without aqueous calibration medium is measured, giving a factory-site dry calibration value $L_D^*$ for each sensor;
    for each selected sensor the luminescence intensity is measured when in contact with at least one of n ($n \geqq 2$) different, aqueous calibrating media, each calibrating medium being used at least once in the calibration of all of the selected sensors, yielding at least one factory-site wet calibration value $L_{iW}^*$ for each sensor;
    from the factory-site dry and wet calibration values of the individual sensors ratio-values $U_i^*=L_{iW}^*/L_D^*$ are computed;
    a suitable function of the general form $L_{rel}=f(u_1, \ldots, u_n, cS$ or $pH)$ describing the shape of the relative sensor characteristic is fitted to the ratio-values $U_i^*$ of all m sensors, resulting in values for the parameters $u_1, \ldots, u_n$;

at the user site
    luminescence intensity is measured for a dry sensor $S_1$ from the plurality of sensors $S_n$ made in the same way, yielding a user-site dry calibration value $L_D$;
    for the sensor $S_1$ in contact with the aqueous sample medium the luminescence intensity $L_{iW}$ is measured, yielding a luminescence measurement value;
    the luminescence measurement value $L_{iW}$ is scaled by the dry value $L_D$, resulting in a ratio-value $U_i$, and the analyte concentration is computed by entering the ratio-value $U_i$ into the equation of the general form $L_{rel}=f(u_1, \ldots, u_n, cS$ or $pH)$ and solving for cS or pH (cS or $pH=f(u_1, \ldots, u_n, L_{rel})$).

It should be noted that in actual sample measurement at the user site only the last three steps have to be performed, since the values resulting from factory-site calibration are supplied with the sensor in suitable form, e.g. as a lot-specific calibration information encoded in a bar-code, a magnetic or electronic code carrier or a ROM-Key.

The variant described in 2.2 has certain advantages, especially if the parameters of the characteristic are obtained in factory-site calibration not only from one sensor $S_0$ but, more realistically, from a statistically representative number of sensors and assigned to the totality of sensors.

EXAMPLE 3

In this example the chemical synthesis of indicator dyes suitable for the present invention, their immobilization to cellulosic fibers, the preparation of dry optical sensor discs

|  | m selected sensors | m dry calibrat. values $t_i$ | n calibrat. media | k wet calibration values $k_{ij}$ | k ratios $k_{ij}/t_i$ |
|---|---|---|---|---|---|
| 1.) m = 1, n = 2, k = 2 | 1 | $t_1$ | 2 | $k_{11}, k_{12}$ | $k_{11}/t_1, k_{12}/t_1$ |
| 2.) m = 3, n = 3, k = 9 | 3 | $t_1, t_2, t_3$ | 3 | $k_{11}, k_{12}, k_{13}$ $k_{21}, k_{22}, k_{33}$ $k_{31}, k_{32}, k_{33}$ | $k_{11}/t_1, k_{12}/t_1, k_{13}/t_1,$ $k_{21}/t_2, k_{22}/t_2, k_{23}/t_2,$ $k_{31}/t_3, k_{32}/t_3, k_{33}/t_3$ |
| 3.) m = 2, n = 5, k = 6 | 2 | $t_1, t_2$ | 5 | $k_{11}, k_{12}, k_{13}$ $k_{23}, k_{24}, k_{25}$ | $k_{11}/t_1, k_{12}/t_1, k_{13}/t_1$ $k_{23}/t_2, k_{24}/t_2, k_{25}/t_2$ | and pH, Na$^+$, K$^+$ and Ca$^{++}$ measurements using the so obtained optical sensors are described.

3.1. Synthesis of the pH-Sensitive Luminescent Dye A41 with the Formula

Chemicals

DCM (dichlormethane): Riedel de Haen 24233>99%; TFA (trifluoracetic acid): Fluka 91700>98%; NHS (N-hydroxysuccinimide): Fluka 56480>97%; DIC (diisopropylcarbodiimide): Fluka 38370>98%; DMAP (4-dimethylaminopyridine): Fluka 39405>98%; DIPEA (diisopropyl-ethylamine): Fluka 03440>98%; acetonitrile: Merck-HPLC-grade; 4-aminomethyl benzoic acid: Fluka: 08400>98%; SOCl$_2$: Fluka: 88950>99%; EtOH abs.: Riedel de Haen: 32221; TEA (triethylamine): Merck: 808352; SO$_2$Cl$_2$: Fluka: 862212; hydrazine-monohydrate: Fluka: 53850; phthalic anhydride: Fluka: 80020; tyramine hydrochloide: Fluka 93820>97%; NMP (N-methylpyrrolidone): Fluka: 69116; 4-chloro-1,8-naphthalic anhydride: Aldrich: 19,149-3~95%.

Figure 7A:
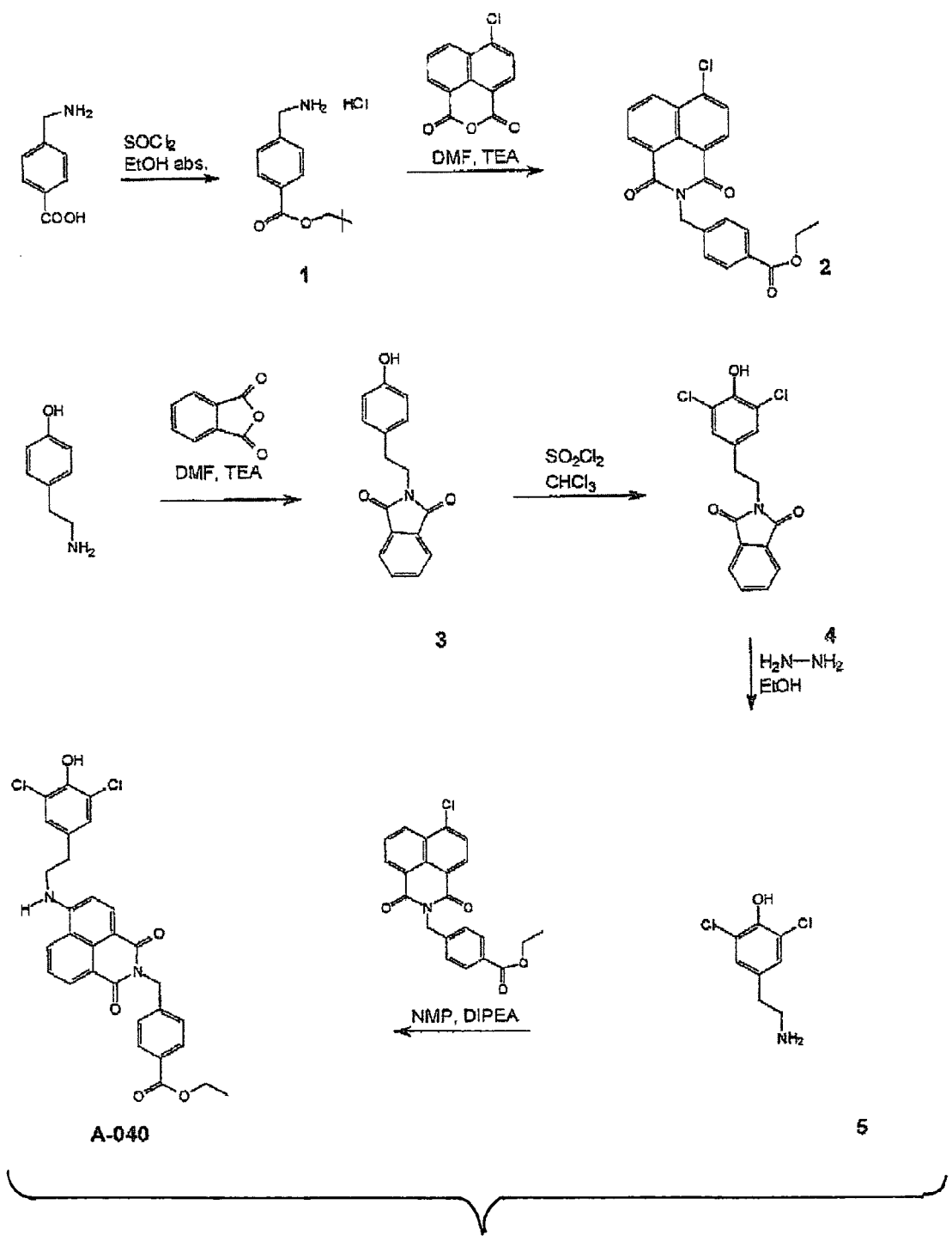
FIG. 7a and FIG. 7b show the synthetic route of luminescent dye A41
Figure 7B:
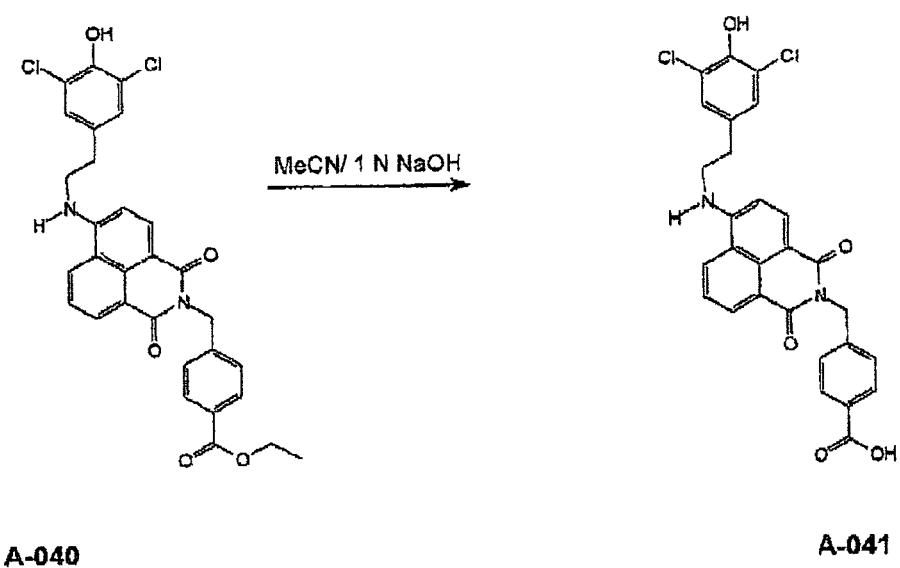

The synthetic route is shown in FIGS. 7a and 7b.

4-Aminomethylbenzoic acid-ethylester hydrochloride (1)

20.0 g (132 mM) of 4-aminomethylbenzoic acid are suspended in 200 ml ethanol (EtOH) abs. and cooled with ice. 28.0 g (17 ml) (236 mM) thionylchloride are added drop by drop. The clear mixture is then refluxed for 3 hours. After cooling to room temperature, EtOH is evaporated. 50 ml of toluene/EtOH 1/1 are added and evaporated three times. The residue is dried to get 27 g of (1).

4-Chloro-naphthalimidyl-methylbenzoic acid-ethylester (2)

20.0 g (93.2 mM) 4-aminomethylbenzoic acid-ethylester hydrochloride, 21.68 g (93.2 mM) 4-Chloro-1,8-naphthalic anhydride and 19.78 g triethylamine (195.5 mM) in 400 ml DMF are heated to 90° C. and stirred overnight. After cooling to room temperature 100 ml H$_2$O are added to precipitate the desired product. The 4-Chloro-naphthal-imidyl-methylbenzoic acid-ethylester (2) is recrystallized from EtOH. Yield: 15.8 g.

The HPLC (Vydac 10-90-15) shows a single peak at t=14.04 and the mass peak

MH$^+$=394.8 (M=393.82) is found in the maldi tof mass spectrum.

Tyraminephthalimide (3)

29.6 g (200 mM) phthalic anhydride, 34.73 tyramine hydrochloride (200 mM) and 27.7 ml triethylamine (200 mM) are heated to 115° C. for 4 hours. After cooling to room temperature, the mixture is poured to 1.5 l ice water. The precipitate (3) is filtered and washed with water. Yield: 45 g

Dichlorotyraminephthalimide (4)

15.35 g (57 mM) tyraminphthalimide (3) are added slowly and in portions to 24.75 g (170 mM) boiling sulfuryl chloride and 75 ml CHCl$_3$. Refluxing is continued till the mixture becomes clear. Then the solution is stirred openly at room temperature overnight to remove sulfuryl chloride. The solvent is removed by evaporation and the crude product (4) is recrystallized from 75 ml MeOH. Yield: 7.2 g.

Dichlorotyramine (5)

7.2 g dichlorotyraminephthalimide (4) and 1.6 ml hydrazine monohydrate are refluxed in 170 ml EtOH abs. overnight. After cooling to room temperature, the precipitate is filtered off. The crude product (5) is not purified for further synthesis.

A-040:

A mixture of 1.5 g (7.26 mM) dichlorotyramine (5), 2.85 g 4-chloronaphthalimidylmethyl-benzoic acid ethylester (2) and 4 ml DIPEA in 150 ml NMP is heated to 90° C. for 4 days.

After cooling to room temperature, 1.5 l water and 7 ml acetic acid (AcOH) are added. The precipitate is filtered off and dissolved in 400 ml CHCl$_3$. The organic layer is extracted with 0.5 N NaOH three times and the NaOH-layer is acidified with 6N HCl. The water layer is extracted with ethyl acetate and the organic layer containing the dye is dried over MgSO$_4$. Solvent is removed by evaporation.

Finally the crude A-040 is purified via dry flash silica gel column chromatography.

Gradient: Petrolether petrolether/ethyl acetate 9/1; petrolether/ethyl acetate 8/2; petrolether/ethyl acetate 7/3; petrolether/ethyl acetate 1/1

The HPLC (Vydac: 10-90-15) shows a single peak at t=13.42 min and the mass peak M=563 (M=563) is found by maldi tof measurement.

A-041:

A-040 is dissolved in 50 ml acetonitrile and 50 ml 1N NaOH. The solution is warmed up to 60° C. and stirred for 1 hour. Then the solution is acidified with HCl and extracted with ethyl acetate. The ethyl acetate layer containing the dye is washed with water three times. After drying the organic layer over MgSO$_4$, the solvent is removed by evaporation. Yield: 350 mg.

The HPLC (Vydac: 10-90-15) shows a single peak at t=11.3 min and the mass peak MH$^+$=535.4 (M=534.4) is found by maldi tof measurement.

3.2. Synthesis of the Na$^+$ Sensitive Luminescent Dye 4-{4'-[4''-C-[aza-15-crown-5]-3''-Methoxyphenyl-ethylamino]-1',8'-napthylamidyl-methyl}benzoic acid The Na$^+$ sensors used are described in U.S. Pat. No. 5,952,491 (Leiner et. al)

An exact description of the preparation of the Na$^+$ sensitive PET indicator dye as well as spectrum and measurement data of the sensors may be found in Anal. Chem. 75, 549-555, 2003 He et al., "A fluorescent chemo sensor for sodium based on photo induced electron transfer".

3.3. Synthesis of the K$^+$ Sensitive Luminescent Dye

The K$^+$ sensors used are described in U.S. Pat. No. 6,211,369 (He et al.).

An exact description of the preparation of the K$^+$ sensitive PET indicator dye as well as spectrum and measurement data of the sensors may be found in the publication J. Am. Chem. Soc. 125, 1468-1469, 2003, supporting information, He et al., "A fluorescent sensor with high selectivity and sensitivity for potassium in water".

3.4. Synthesis of the Ca$^{++}$ Sensitive Luminescent Dye

The Ca$^{++}$ sensitive indicator dye is prepared as described in U.S. Pat. No. 6,171,866 (He et al.).

3.5. Preparation of Amino Cellulose Fibers

Amino cellulose fibers is prepared as described in SU 1,028,677, CA 99.177723b.

3.6. Immobilization of the pH, Na$^+$, K$^+$ und Ca$^{++}$ Sensitive Indicator Dyes on Amino Cellulose Fibers The immobilization of all four dyes to amino cellulose fibers is carried out analogously to example 18 in U.S. Pat. No. 6,211,359 (He et al.).

3.7. Establishing a Known Ratio of the Respective Indicator Species A and B

In order to establish a known ratio V (eqn. 6) of the species A and B, after immobilization of the indicator dyes the fibers carrying the indicator are washed with an aqueous medium which contains the relevant analyte in suitable concentration, such that after equilibrium is reached (eqn. 1 and 2) the desired ratio of the concentrations of the indicator species A and B is established. Subsequently the fibers are rinsed by short contact with de-ionized water and dried, which does not change the established ratio of the two indicator species.

Alternatively it is also possible to produce the complete sensors first and wash them with an aqueous medium containing the relevant analyte in suitable concentration, such that after equilibrium is reached (eqn. 1 and 2) the desired ratio of the concentrations of the indicator species A and B is established, and to dry the sensors subsequently.

To establish a certain ratio of the species A and B it is for instance possible in the case of pH sensors to equilibrate the sensors or the raw materials (e.g. fibers carrying the indicator, particles etc.) with acids, bases, or buffers with known pH.

In the case of ion-sensors the raw materials resp. the sensors can be equilibrated with aqueous solutions containing the ion to be determined in suitable concentration.

Alternatively it is possible in the case of PET indicator dyes described in U.S. Pat. No. 5,952,491 (Leiner et al.), U.S. Pat. No. 6,211,359 (He et al.), U.S. Pat. No. 6,171,866 (He et al.) to establish with acids (e.g. HCl) or pH-buffered solutions a certain ratio of the two species A and B in the absence of the ion to be determined. This is possible because the aromatically bound nitrogen atoms of the ionophore moiety are pH-active. The pK value of the aromatically bound N atoms is approximately 5, for instance. In contact with acidic liquids the nitrogen is protonated and the PET effect is eliminated. The luminescence of the protonated species corresponds to the luminescence of species B, to which the analyte (the ion to be determined) is bound. Thus it is possible in the case of certain luminescence indicators for metal cations having pH-active ionophore moieties, to establish a predetermined ratio of the weakly and strongly luminescent indicator species by means of protons. The proton acts as analyte-analogon.

3.8. Fabrication of Optical Sensors (Sensor Discs) of H$^+$ (pH), Na$^+$, K$^+$ and Ca$^{++}$ Sensitive Optical Sensors The fabrication of the four sensors was carried out analogously to example 19 in U.S. Pat. No. 6,211,359 (He et al.).

0.5 g sieved (25 μm) cellulose powder with immobilized indicator from Example 3.7 is suspended in 9.5 g of a solution of 10% hydrophilic polyether-polyurethane-copolymer in 90% ethanol-water for 16 h. Such polyether-polyurethane copolymers can be obtained for example from CardioTech International, Inc. Woburn, Mass., U.S.A. The resultant homogeneous dispersion is coated on a polyester foil (Melinex foil, ICI America) with a final dry thickness of 10 μm. This foil is overcoated with 3% carbon black in a solution of 10% polyether-polyurethane copolymer in 90% ethanol-water with a dry thickness of 5 μm. Then small discs of 3 mm diameter are punched out.

Methods of preparing sensor discs were described by M. J. P. Leiner and P. Hartmann in Sensors and Actuators B, 11 (1993), 281-189 ("Theory and Practice in optical pH sensing").

3.9. Fabrication of Disposable Measuring Cells Containing an Array of H$^+$ (pH), Na$^+$, K$^+$ and Ca$^{++}$ sensitive optical sensors The sensor discs of example 3.8 are incorporated in disposable plastic measuring cells. The cells consist of injection moulded top and bottom parts, a channel for passage of calibrants and sample, sealable inlet and outlet openings. The bottom part has cylindrical cavities for inlay of the sensor discs. After incorporation of the H$^+$ (pH), Na$^+$, K$^+$ and Ca$^{++}$ sensitive sensor discs in the cavities, the bottom and top parts are glued together to form the final measuring cell. Illumination of the respective indicator dye and collection of the longer wavelength luminescence light is carried out through the bottom part of the cell.

After assembly, the disposable cells are placed for several days in closed containers containing an appropriate desiccant to allow the sensors to further dry down to the desired level of humidity. After drying, the inlet and outlet openings are sealed and the cells are stored in closed containers along with an appropriate desiccant until use.

Alternatively it is also possible to seal the inlet and outlet openings immediately after assembly of the disposable cells and to store the cells in closed desiccant containing packaging until use. In such case, drying occurs through the sealing material and/or through the plastic materials. Due to the low water permeability of plastics, the drying process will take longer (i.e., weeks).

Methods of preparing disposable measuring cells are described by M. J. P. Leiner in Sensors and Actuators B, 29 (1995), 269-173 ("Optical sensors for in vitro blood gas analysis").

3.10. Dry and Wet Measurements of Disposable Cells in a Measuring Setup

For measurement, the disposable cells are introduced into a thermostated measuring chamber impervious to light. The inlet and outlet openings are connected to a fluidic system to allow passage of aqueous solutions having different pH-values and/or different concentration of alkali ions.

For each channel (sensor) the optical measuring system consists of a blue LED as the light source, a photodiode as the detector, optical filters for selecting the wavelengths, an optic arrangement for conducting the excitation light into the indicator layer of the sensor and for conducting the emission light to the photo detector as well as a device for electronic signal processing. At the excitation end an interference filter (peak transmission at 480 nm) is utilized and at the emission end a 520 nm cut-off filter.

3.11. Measurement Results with pH Sensors

Figure 3:
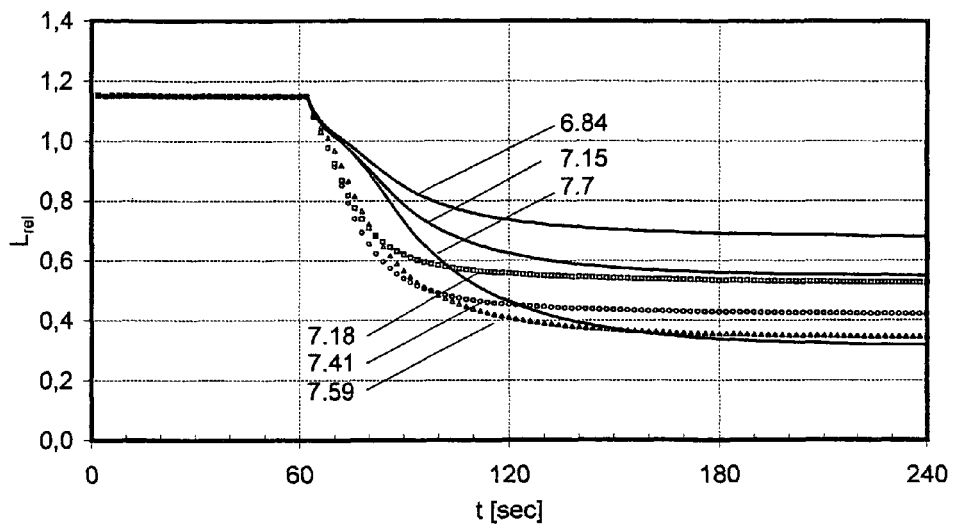
FIG. 3 shows the response curves (scaled relative luminescence intensity $L_{rel}$ as a function of time t in sec.) of six individual pH sensors.

In FIG. 3 the response curves (luminescence intensity as a function of time) of six individual pH sensors—selected from a plurality of sensors made in the same way—are shown as functions of time t (measured in seconds) in the dry state and during the equilibration phase with aqueous fluids. The intensity values are measured in time intervals of 2 seconds.

For this group of sensors (see item 3.7) the material carrying the indicator (cellulose fibers) is washed with HCl (pH~3) prior to introducing it into the sensor layer. Thus only species B is present in the dry sensors of this group. The ratio $V=cB/cD$ therefore equals 1 in the dry sensor (eqn. 6).

Following the insertion of the sensors, which are stored in contact with a dry gaseous medium, into the measuring device, they are thermostated at 37° C. (not shown), illuminated, and the dry luminescence intensity is measured (this is the time interval 0-60 s). Then the gaseous medium is replaced by the aqueous fluid (different for each sensor). During the time interval 60-240 s equilibration of the sensors to the pH-value of the fluid occurs.

The intensities measured with different dry sensors are different (not shown). For clarity of presentation the response curves of FIG. 3 are scaled in such a way that the mean values of the dry intensities shown have the value 1.15. This value 1.15 represents the ratio $R_{mD/W}$ (of eqn. 13).

Scaling in this context means: the intensity values measured at intervals of 2 seconds are multiplied by a factor (=1.15/average of the dry intensities over the time interval 0-60 s).

Two groups of sample fluids are used.

The group with pH-values 7.18, 7.41, 7.59 consists of aqueous electrolyte fluids which are typically used for control and calibration purposes in the determination of blood parameters (see e.g. U.S. Pat. No. 6,174,728).

The group with pH-values 6.84, 7.15, 7.18 consists of HEPES buffers with physiological values of $Na^+$, $K^+$, $Ca^{++}$, and $Cl^-$.

During the time interval 60-240 s two processes occur simultaneously, i.e. wet-up and equilibration to the pH-value of the fluid.

In the time interval 230-240 s these processes essentially have terminated. The luminescence intensity in this interval is the wet intensity of the sample.

From the shape of the curves it can be observed that the kinetics of the equilibration process indeed depend on the type of sample.

Figure 4:
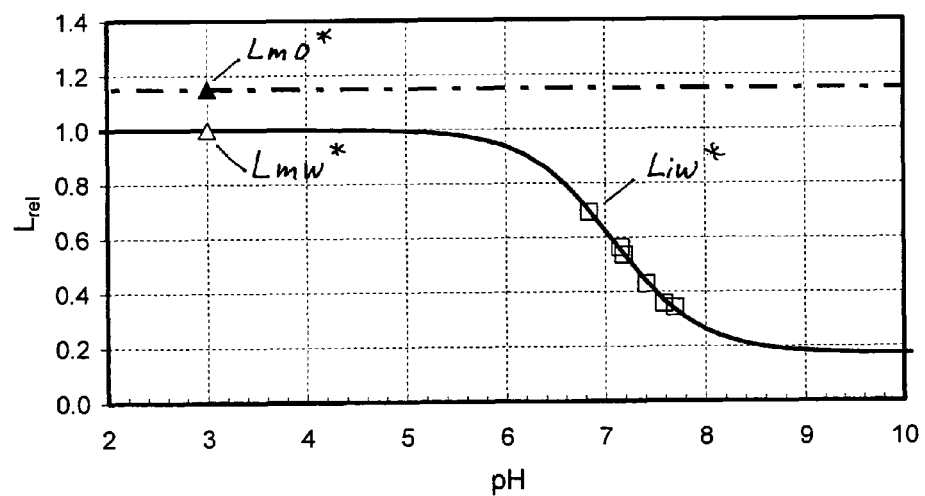
FIG. 4 shows the scaled luminescence values in accordance with FIG. 3 as functions of pH-value.

In the diagram of FIG. 4 the scaled luminescence values of FIG. 3 are plotted against the pH-values on the abscissa.

The triangular symbols indicate that in the example the protonated species B is exclusively present in the dry state. The dark triangles, respectively the dashed lines, denote the dry calibration values $L_{mD}^*$ and $L_{mD}$. In the dry state there is no pH-dependence! The light triangle denotes the wet calibration value $L_{mW}^*$ when only the protonated species B is present.

The square symbols denote the intensities $L_{iW}^*$ of the individual sensors after equilibration, scaled by the dry values. The solid line is the relative characteristic according to eqn. 10, with $L_{mW}^*$ equal to 1.

The parameters q and pK of the characteristic result from fitting eqn. 10 to the measurement data represented by the square symbols by the method of least squares. The approximation yields the result: q=0.17, pK =7.08.

With the species B present the dry intensities $L_{mD}^*$ and $L_{mD}$ are greater by a factor $R_{mD/W}$=1.15 than the wet intensities $L_{mW}^*$ and $L_{mW}$.

In accordance with example 1.1, the relative characteristic (eqn. 10) is given by the parameters $L_{mW}$=1, q=0.17, pK=7.08, with the ratio $R_{mD/W}$=1.15.

Figure 5:
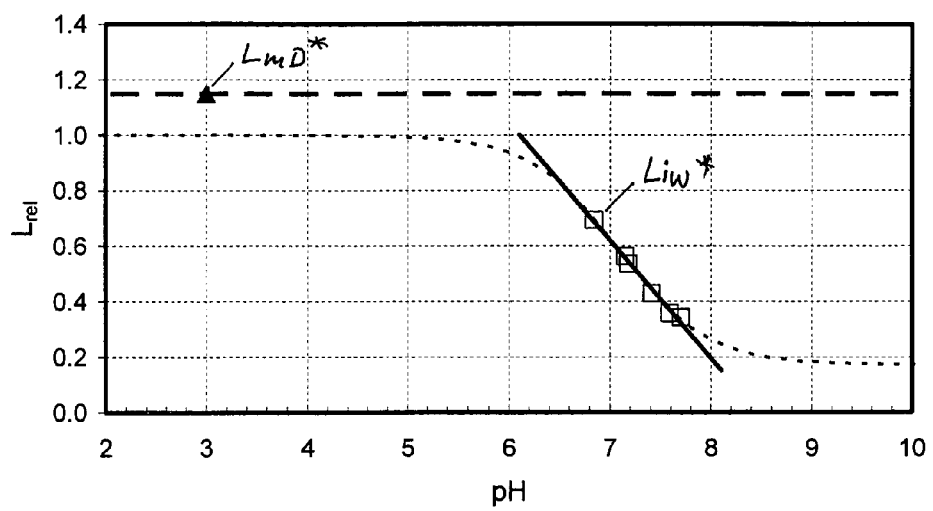
FIG. 5 shows a diagram as in FIG. 4 with the difference that the relative characteristic (solid curve) is represented by the linear relationship $L_{rel} = u_1 + u_2 \text{pH}$.

The diagram of FIG. 5 corresponds to that of FIG. 4, the difference being that the equation $L_{rel}=u_1+u_2 \cdot pH$ is used to represent the relative characteristic (solid line). For comparison reasons, the relative characteristic from FIG. 4 is shown as a dashed line.

In accordance with example 2.2, the relative characteristic is given by the parameters $u_1$=3.59 and $u_2$=-0.42. In the limited pH range 6.3-7.6 the shape of this characteristic approximates that of FIG. 4.

Figure 6:
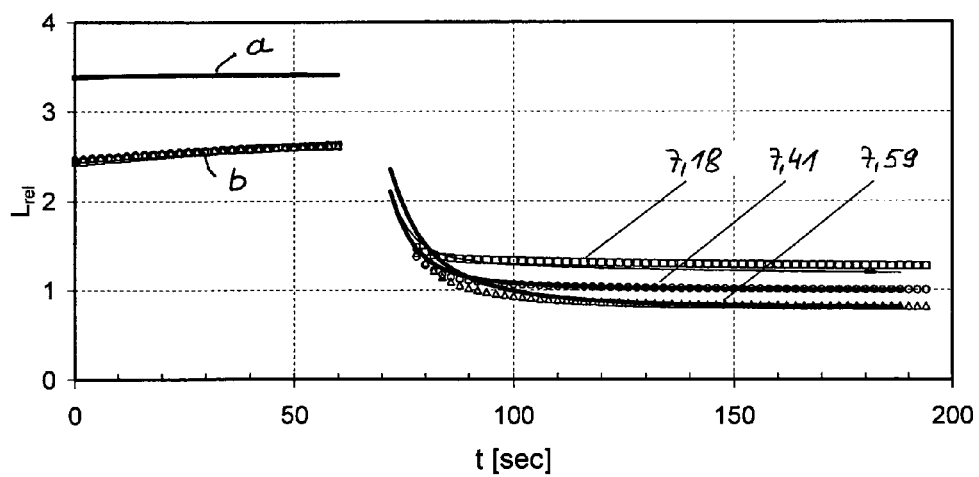
FIG. 6 shows the scaled luminescence intensities $L_{rel}$ of two groups of sensors with different pretreatment (solid line and symbols) as functions of time t.

FIG. 6 shows the luminescence intensities $L_{rel}$ of two groups of sensors with differing pre-treatment (group a: solid lines, group b: symbols). In group a (see example 3.7) the carrier of the indicator (cellulose fibers) is washed with HCl (pH~3) prior to being introduced into the sensor layer. As a consequence only the species B is present in the dry pH sensors of this group. In group b (see example 3.7) the carrier of the indicator (cellulose fibers) is washed with phosphate buffer (pH~7.4) prior to introduction into the sensor layer. Therefore a ratio V=cB/cD (eqn. 6) of the two indicator species is realized in the dry sensors of this group.

After insertion of the sensors stored in contact with a dry gaseous medium into the measuring device they are thermostated to 37° C. (not shown), illuminated with blue light, and the luminescence intensity is measured as a function of time at intervals of 2 seconds. In the time interval 0-60 s the sensors were dry. In the interval 60-70 s the gaseous medium is replaced by the sample fluid (no measurements are taken during this time). In the time interval 70-200 s wet-up and equilibration to the pH-value of the sample occurs.

Wet-up and equilibration of the 3 sensors of each group is performed with aqueous electrolyte fluids (pH-values 7.18, 7.41, 7.59), which are typically used for control and calibration purposes in devices for the determination of blood parameters (described in U.S. Pat. No. 6,174,728).

The measured intensities of the different dry sensors are different (not shown). The measured intensities of each curve in FIG. 6 are normalized in two steps.

Step 1: the last 10 values measured on each dry sensor are averaged. Then all measured values of the curve are divided by the mean value.

Step 2, group a: the last 10 values measured on the wet sensor of the curve with pH-value 7.41 are averaged. Then all three curves of group a are divided by this mean value.

Step 2, group b: the three curves of group b are treated analogously to group a.

From the presentation chosen it can be seen that after equilibration the relative intensities of both groups are essentially the same and correlate with the pH-values of the sample fluids.

Furthermore it is evident that (as was to be expected) the dry intensity of group a is greater than that of group b: both groups have the same amount of indicator dye; in group a the dye is present in the strongly luminescent species B, while in group b there is a mixture of the strongly and the weakly luminescent species.

Table 1: contains the measured dry and wet intensities of group a as presented in FIG. 6. In the dry pH sensors of this group only species B is present. The wet/dry intensity ratios are obtained by dividing the measured wet values by the corresponding measured dry value (e.g. 463944/172253=2.69).

TABLE 1

| pH | Measured Dry Intensity | Measured Wet Intensity | Dry/Wet Intensity Ratio |
|---|---|---|---|
| 7.18 | 463944 | 172253 | 2.69 |
| 7.41 | 475324 | 146897 | 3.24 |
| 7.59 | 460287 | 125670 | 3.66 |

Table 2: contains the wet values of group a as presented in FIG. 6, normalized by the dry value. The dry values are normalized to 1 (e.g. 463944/463944=1). The normalized wet values are obtained by dividing the measured wet values of table 1 by the corresponding dry value of table 1 (e.g. 172253/463944=0.371). The dry/wet intensity ratios are obtained by dividing the normalized dry value by the normalized wet values (e.g. 1/0.371=2.69).

TABLE 2

| pH | Dry intensity normalized | Normalized Wet Intensity | Dry/Wet Intensity Ratio |
|---|---|---|---|
| 7.18 | 1 | 0.371 | 2.69 |
| 7.41 | 1 | 0.309 | 3.24 |
| 7.59 | 1 | 0.273 | 3.66 |

A comparison of table 1 and table 2 shows that equivalent dry/wet ratios are obtained, regardless of whether the ratios are directly obtained by dividing the measured wet values by the measured dry values or whether the measured wet values are first normalized by the dry values and the ratios are then computed by dividing the normalized values.

Normalization permits comparison in graphic form between measured curves or measured data of sensors with differing luminescence intensity.

Table 3: contains the wet values of group b as presented in FIG. 6, normalized by the dry value. In the dry pH sensors of this group both species A and B are present.

TABLE 3

| pH | Normalized Dry Intensity | Normalized Wet intensity | Dry/Wet Intensity Ratio |
|---|---|---|---|
| 7.18 | 1 | 0.503 | 1.99 |
| 7.41 | 1 | 0.399 | 2.51 |
| 7.59 | 1 | 0.338 | 2.96 |

3.12. Measurement Results with $Na^+$ Sensors

Table 4: Normalized dry and wet intensities of sensors for determining $Na^+$-ion concentration in aqueous samples.

TABLE 4

| $cNa^+$ [mmol/l] | Normalized Dry Intensity | Normalized Wet Intensity | Dry/Wet Intensity Ratio |
|---|---|---|---|
| 122 | 1 | 0.290 | 3.45 |
| 143 | 1 | 0.319 | 3.13 |
| 155 | 1 | 0.338 | 2.96 |

3.13. Measurement Results with $K^+$ Sensors

Table 5: Normalized dry and wet intensities of sensors for determining $K^+$-ion concentration in aqueous samples.

TABLE 5

| $cK^+$ [mmol/l] | Normalized Dry Intensity | Normalized Wet Intensity | Dry/Wet Intensity Ratio |
|---|---|---|---|
| 3.0 | 1 | 0.346 | 2.89 |
| 4.9 | 1 | 0.383 | 2.61 |
| 5.9 | 1 | 0.401 | 2.49 |

3.14. Measurement Results with $Ca^{++}$ sensors

Table 6: Normalized dry and wet intensities of sensors for luminescence-optical determination of ionized $Ca^{++}$ in aqueous samples.

TABLE 6

| $cCa^{++}$ [mmol/l] | Normalized Dry Intensity | Normalized Wet Intensity | Dry/Wet Intensity Ratio |
|---|---|---|---|
| 1.55 | 1 | 0.317 | 3.15 |
| 1.23 | 1 | 0.345 | 2.90 |
| 0.84 | 1 | 0.359 | 2.79 |

3.16. Measurement Results with $Cl^-$ Sensors

Table 7: Normalized dry and wet intensities of sensors for determining $Cl^-$-ion concentration in aqueous samples.

TABLE 7

| $cCl^-$ [mmol/l] | Normalized Dry Intensity | Normalized Wet Intensity | Dry/Wet Intensity Ratio |
|---|---|---|---|
| 88 | 1 | 0.386 | 2.59 |
| 106 | 1 | 0.352 | 2.84 |
| 119 | 1 | 0.321 | 3.12 |

The Cl⁻ sensors used are described in U.S. Pat. No. 6,613,282 (Huber).

The invention claimed is:

1. A method for the determination of the concentration of a nonvolatile analyte present in an aqueous sample medium using an optical sensor which contains in at least one sensor layer an immobilized luminescent indicator dye that exhibits luminescence in a dry state when excited and that has optical characteristics that vary with the concentration of the analyte contained in the aqueous sample medium, the method comprising:

calibrating the optical sensor by a single-point calibration having only one calibration step, the only one calibration step comprising measuring luminescence of the optical sensor as a dry optical sensor without the use of calibrating media, yielding a user-site dry calibration value;

obtaining a luminescence measurement value of the optical sensor as a wet optical sensor in contact with the aqueous sample medium; and deducing the concentration of the non-volatile analyte from the luminescence measurement value, the user-site dry calibration value, and a predetermined wet to dry relationship that is supplied together with the optical sensor and is derived from a factory-site wet calibration value and a factory-site dry calibration value.

2. The method of claim 1, wherein:

a) the wet to dry relationship is derived by:
   i. choosing a representative number of sensors $S_0$ from a batch or lot of sensors consisting of N sensors $S_n$, each made in the same way, where N>=1 and each n is from 1 to N;
   ii. measuring luminescence of each of the chosen sensors $S_0$ as dry sensors $S_0$, yielding factory-site dry calibration values;
   iii. subsequently measuring luminescence of each of the chosen sensors $S_0$ as wet sensors $S_0$ in subsequent contact with at least two aqueous calibrating media with known, different concentrations of the non-volatile analyte, yielding factory-site wet calibration values; and
   iv. obtaining a wet to dry relationship of the sensors $S_0$ from the factory-site wet calibration values and the factory-site dry calibration values, which wet to dry relationship is taken as the wet to dry relationship for all sensors $S_n$ made in the same way; and b) the optical sensor is a sensor $S_1$ selected from the sensors $S_n$ made in the same way, whereby:
   i. measuring luminescence of the optical sensor as a dry optical sensor comprises measuring luminescence of the sensor $S_1$ as a dry sensor $S_1$ without the use of calibrating media, yielding the user-site dry calibration value;
   ii. obtaining the luminescence measurement value comprises obtaining a luminescence measurement value of the sensor $S_1$ as a wet sensor $S_1$ in contact with the aqueous sample medium; and
   iii. deducing the concentration of the non-volatile analyte comprises computing the concentration of the non-volatile analyte present in the aqueous sample medium from the luminescence measurement value, the user-site dry calibration value, and the wet to dry relationship for all the sensors $S_n$ made in the same way.

3. The method of claim 2, wherein the wet to dry relationship comprises a relative characteristic and a ratio value, the method further comprising in step a) iv. obtaining from the factory-site wet calibration values the relative characteristic of the sensors $S_0$, which relative characteristic is taken as the relative characteristic for all sensors $S_n$ made in the same way; and deriving the ratio value from the factory-site wet calibration values and the factory-site dry calibration values, which ratio value is taken as the ratio-value for all sensors $S_n$ made in the same way; and in step b) iii. computing the concentration of the nonvolatile analyte present in the aqueous sample medium from the luminescence measurement value, the user-site dry calibration value, the relative characteristic and the ratio value obtained at the factory site.

4. The method of claim 3, further comprising:

in step a) i.
   choosing sensors $S_0$, in each of which the luminescent indicator dye is present in the form of a first luminescent species and a second luminescent species, the analyte or an analyte-analogue being bound to the second luminescent species but not to the first luminescent species, in step a) ii.
   obtaining from the luminescence measurements factory-site dry calibration values $L_{mD}*$, wherein each $L_{mD}*$ represents the maximum intensity value measured from a corresponding one of the chosen sensors $S_0$, in step a) iii.
   choosing the concentration of the non-volatile analyte for at least one of the aqueous calibrating media such that after wet-up and equilibration essentially only the second species is present and measuring factory-site wet calibration values $L_{mW}*$, wherein each $L_{mW}*$ represents the maximum luminescence intensity value measured from a corresponding one of the chosen sensors $S_0$, in step a) iv.
   computing a ratio-value $R_{mD/W}$ from the factory-site dry calibration values $L_{mD}*$ and the factory-site wet calibration values $L_{mW}*$, wherein $R_{mD/W} = L_{mD}*/L_{mW}*$, in step b) i.
   obtaining a user-site dry calibration value $L_{mD}$, wherein $L_{mD}$ represents the maximum luminescence of the dry sensor $S_1$ and in step b) iii.
   computing a user-site scaling factor $L_{mW}$ from $L_{mD}$ and the ratio-value $R_{mD/W}$, wherein $L_{mW} = L_{mD}/R_{mD/W}$, and determining the concentration of the nonvolatile analyte from the luminescence measurement value, the user-site scaling factor $L_{mW}$ and the relative characteristic.

5. The method of claim 3, further comprising:

in step a) i.
   choosing sensors $S_0$, in each of which the luminescent indicator dye is present in the form of a first luminescent species and a second luminescent species, the analyte or an analyte-analogue binding to the second luminescent species but not to the first luminescent species, and the ratio V of the concentration (cB) of the second luminescent species relative to the total concentration (cD) of the luminescent indicator dye (V=cB/cD) is known, wherein cD is the sum of the concentration (cA) of the luminescent indicator dye present in the form of the first luminescent species and the concentration (cB) of the luminescent indicator dye present in the form of second luminescent species, and wherein $0.1 < V < 0.9$, in step a) ii.
　　obtaining from the luminescence measurements factory-site dry calibration values $L_D^*$, wherein each $L_D^*$ represents the luminescence of a corresponding one of the chosen sensors $S_0$, in step a) iii.
　　choosing the concentration of the non-volatile analyte for at least one of the aqueous calibrating media such that after wet-up and equilibration essentially only the second luminescent species is present and measuring factory-site wet calibration values $L_{mW}^*$, in step a) iv.
　　computing a ratio-value $R_{D/W}$ from the factory-site dry calibration values $L_D^*$ and the factory-site wet calibration values $L_{mW}^*$, wherein each $L_{mW}^*$ represents the maximum luminescence intensity value measured from a corresponding one of the chosen sensors $S_0$, and $R_{D/W}=L_D^*/L_{mW}^*$, in step b) i.
　　obtaining a user-site dry calibration value $L_D$ as the user-site dry calibration value, wherein $L_D$ represents the luminescence of the dry sensor $S_1$, and in step b) iii.
　　computing a user-site scaling factor $L_{mW}$ from $L_D$ and the ratio-value $R_{D/W}$, wherein $L_{mW}=L_D/R_{D/W}$, and determining the concentration of the non-volatile analyte from the luminescence measurement value, the user-site scaling factor $L_{mW}$ and the relative characteristic.

6. The method of claim 3, further comprising:

in step a) i.
　　choosing sensors $S_0$, in each of which the luminescent indicator dye is present in the form of a first luminescent species and a second luminescent species, the non-volatile analyte or an analogue thereof binding to the second luminescent species and not binding to the first luminescent species, the ratio V of the concentration (cB) of the second luminescent species relative to the total concentration (cD) of the luminescent indicator dye (V=cB/cD) being known, wherein cD is the sum of the concentration (cA) of the luminescent indicator dye present in the form of the first luminescent species and the concentration (cB) of the luminescent indicator dye present in the form of the second luminescent species, and 0.1<V<0.9, in step a) ii.
　　obtaining from the luminescence measurements factory-site dry calibration values $L_D^*$, wherein each $L_D^*$ represents the luminescence of a corresponding one of the chosen sensors $S_0$, in step a) iii.
　　measuring luminescence intensity of the sensors $S_0$ in at least two aqueous calibrating media with known, different concentrations $cS_i$, of the non-volatile analyte yielding at least two factory-site wet calibration values $L_{iw}^*$, wherein each $L_{iw}^*$ refers to a respective luminescence intensity $L_w^*$ of a corresponding one of the sensors $S_0$ in a corresponding one of the at least two aqueous calibrating media and i is an index defining value pairs each consisting of exactly one factory-site wet calibration value $L_{iw}^*$ and exactly one concentration $cS_i$, of the non-volatile analyte, and in step a) iv.
　　obtaining the relative characteristics and the factory-site wet calibration values $L_{mW}^*$ of the sensors $S_0$ from the value pairs $L_{iw}^*$, $cS_i$, according to $$L_{mW}^*=L_{iW}^*(1+(q-1)/(1+cS_i/K_d)),$$

wherein the parameter values q and $K_d$ are known, parameter value q represents the ratio of luminescence intensity of pure first luminescent species to the luminescence intensity of pure second luminescent species at the concentration $cS_i$ and parameter value $K_d$ represents a dissociation constant of the luminescent indicator dye, and
　　computing therefrom the relative characteristic valid for all sensors $S_n$ made in the same way, and
　　computing a ratio-value $R_{D/W}$ from the factory-site dry calibration values $L_D^*$ and the factory-site wet calibration values $L_{mW}^*$, wherein $R_{D/W}=L_D^*/L_{mW}^*$, yielding in step b) i.
　　the user-site dry calibration value $L_D$, wherein $L_D$ represents the luminescence of the sensor $S_1$ as a dry sensor $S_1$, and in step b) iii.
　　computing a user-site scaling factor $L_{mW}$ from $L_D$ and the ratio-value $R_{D/W}$, wherein $$L_{mW}=L_D/R_{D/W}, \text{ and}$$

determining the concentration of the non-volatile analyte from the luminescence measurement value, the user-site scaling factor $L_{mW}$ and the relative characteristic.

7. The method of claim 2, further comprising:
in step a) iv obtaining a relative characteristic of the sensors $S_0$ from the factory-site wet calibration values and the factory-site dry calibration values, which relative characteristic is taken as the relative characteristic for all sensors $S_n$ made in the same way; and
in step b) iii. computing the concentration of the nonvolatile analyte present in the aqueous sample medium from the luminescence measurement value, the user-site dry calibration value and the relative characteristic.

8. The method of claim 2, further comprising:
in step a) iv computing ratio-values from the factory-site wet calibration values and the factory-site dry calibration values; and
　　obtaining a relative characteristic of the sensors $S_0$ from the ratio-values, which relative characteristic is taken as the relative characteristic for all sensors $S_n$ made in the same way; and
in step b) iii. computing a user-site ratio-value from the user-site dry calibration value and the luminescence measurement value; and
　　computing the concentration of the non-volatile analyte present in the aqueous sample medium from the user-site ratio-value and the relative characteristic.

9. The method of claim 7, wherein:
in step a) i. the representative number is m, where m>=1, and
in step a) ii. m factory-site dry calibration values $t_i$, with i=1 to m, are obtained from the chosen sensors $S_0$ as dry sensors $S_0$, and that
in step a) iii. from the luminescence measurements of each of the sensors $S_0$ as wet sensors $S_0$ wet calibration values with at least one of n≧2 different aqueous calibration media are taken, each calibration medium being used at least once, such that $k \geq n$ wet calibration values $k_{ij}$, with $j=1$ to $n$, are obtained, and that in step a) iv. ratio-values $k_{ij}/t_i$, are computed from the individual pairs $t_i, k_{ij}$ and the relative characteristic of the sensor $S_0$ is derived from the ratio-values $k_{ij}/t_i$.

10. The method of claim 5, further comprising setting of a predetermined, known ratio $V=cB/cD$ in the sensors $S_n$, wherein the setting comprises washing a substrate carrying the luminescent indicator dye or the sensor with an aqueous washing medium containing the non-volatile analyte or an analyte-analogue in suitable concentration, the predetermined ratio being established after equilibration and being fixed by drying the substrate carrying the luminescent indicator dye or the sensor.

11. The method of claim 10, wherein the optical sensor is a pH sensor and the aqueous washing medium is selected from acids, bases or buffers with known pH-values.

12. The method of claim 10, wherein for each dry sensor of a plurality of sensors $S_n$ made in the same way the ratio of the concentration of the first luminescent species to the concentration of the second luminescent species is essentially the same and constant over time.

13. The method of claim 1, further comprising storing the optical sensor in the dry state at a factory site and at a user site prior to calibrating the optical sensor.

14. The method of claim 1, wherein at least one optical sensor for determination of the nonvolatile analyte is employed in combination or in a joint sensor configuration with sensors for determining the concentration of volatile analytes.

* * * * *

UNITED STATES PATENT AND TRADEMARK OFFICE
CERTIFICATE OF CORRECTION

| | | |
|---|---|---|
| PATENT NO. | : 8,158,438 B2 | Page 1 of 1 |
| APPLICATION NO. | : 11/994548 | |
| DATED | : April 17, 2012 | |
| INVENTOR(S) | : Marco Jean-Pierre Leiner and James Kenneth Tusa | |

It is certified that error appears in the above-identified patent and that said Letters Patent is hereby corrected as shown below:

Col. 39, Line 47, "S 1" should read -- S1 --

Col. 40, Line 40, "LmW," should read -- LmW*, --

Col. 40, Line 44, "S1 and" should read -- S1, and --

Col. 42, Line 12, "cSi" should read -- cSi, --

Signed and Sealed this
Thirty-first Day of July, 2012

David J. Kappos
*Director of the United States Patent and Trademark Office*